US009464326B2

(12) United States Patent
Davila

(10) Patent No.: US 9,464,326 B2
(45) Date of Patent: Oct. 11, 2016

(54) TOTAL AND PHOSPHORYLATED IL-1 RECEPTOR-ASSOCIATED KINASE-1 AND IL-1 RECEPTOR-ASSOCIATED KINASE-4 AS A BIOMARKER FOR CANCER PROGRESSION AND CHEMOTHERAPY RESISTANCE

(71) Applicant: University of Maryland, Baltimore, Baltimore, MD (US)

(72) Inventor: Eduardo Davila, Cockeysville, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 76 days.

(21) Appl. No.: 13/804,135

(22) Filed: Mar. 14, 2013

(65) Prior Publication Data

US 2013/0280264 A1 Oct. 24, 2013

Related U.S. Application Data

(60) Provisional application No. 61/614,196, filed on Mar. 22, 2012.

(51) Int. Cl.
| | |
|---|---|
| G01N 33/574 | (2006.01) |
| G01N 33/68 | (2006.01) |
| C07D 235/04 | (2006.01) |
| C12Q 1/68 | (2006.01) |
| A61K 39/395 | (2006.01) |
| A61K 45/06 | (2006.01) |

(52) U.S. Cl.
CPC ....... *C12Q 1/6886* (2013.01); *A61K 39/39558* (2013.01); *A61K 45/06* (2013.01); *G01N 33/57484* (2013.01); *G01N 33/6893* (2013.01); *C07D 235/04* (2013.01); *C12Q 2600/106* (2013.01); *C12Q 2600/158* (2013.01); *G01N 2333/9121* (2013.01); *G01N 2800/52* (2013.01)

(58) Field of Classification Search
CPC ................................................. A61K 31/4184
See application file for complete search history.

(56) References Cited

U.S. PATENT DOCUMENTS 6,355,623 B2 * 3/2002 Seidman et al. ................ 514/45

FOREIGN PATENT DOCUMENTS

WO WO 03/030902 A1 * 4/2003 ......... A61K 31/4184

OTHER PUBLICATIONS

Benedict et al (J. Exp. Medicine, 2001, 193(1) 89-99).*
Jiang et al (JBC, 2003, 278(7) 4763-4769).*
Matsushita et al (FEBS Letters, 1999, vol. 443, pp. 348-352).*
Singh et al. (Glycobiology, 2001, vol. 11, pp. 587-592).*
Interleukin-1 Receptor-Associated-Kinase-1/4 Inhibitor—CAS 509093-47-4—Calbiochem, (EMD Millipore, 2014).*
Equivalent Surface Area Dosage Conversion Factors (DTP/DCTD/NCI/NIH/DHHS http://dtp.nci.nih.gov/, Aug. 2007).*
Leonetti et al. (Int. J. Cancer, 2004 110:767-774).*
Cheng et al. (Biochem. Biophys. Res. Comm. 2007 32:609-616).*
Li et al. (PNAS Apr. 16, 2002 99(8): 5567-5572).*
J. Bohnhorst et al., "Toll-like receptors mediate proliferation and survival of multiple myeloma cells", "Leukemia", 2006, pp. 1138-1144, vol. 20, Publisher: Nature Publishing Group, Published in: www.nature.com/leu.
Zhaodan Cao et al., "IRAK: A Kinase Associated with the Interleukin-1 Receptor", "Science", 1996, pp. 1128-1131, vol. 271, Publisher: American Association for the Advancement of Science, Published in: http://www.sciencemag.org/content/271/5252/1128.abstract?sid=854b0613-d1e0-4379-aba0-60829bd0e426.
Wei Chen et al., "Human 60-kDa Heat-Shock Protein: A Danger Signal to the Innate Immune System", "Journal of Immunology", 1999, pp. 3212-3219, vol. 162, Publisher: American Association of Immunologists, Inc., Published in: http://www.jimmunol.org/content/162/6/3212.
Ni Cheng et al., "Cutting Edge: TLR2 Is a Functional Receptor for Acute-Phase Serum Amyloid A", "Journal of Immunology", 2008, pp. 22-26, vol. 181, Publisher: American Association of Immunologists, Inc., Published in: http://www.jimmunol.org/content/181/1/22.
Clett Erridge, "Endogenous ligands of TLR2 and TLR4: agonists or assistants?", "Journal of Leukocyte Biology", 2010, pp. 989-999, vol. 87, No. 6, Publisher: Society for Leukocyte Biology, Published in: http://www.jleukbio.org/content/87/6/989.full.pdf+html.
Brandt L. Esplin et al., "Chronic Exposure to a TLR Ligand Injures Hematopoietic Stem Cells", "Journal of Immunology", 2011, pp. 5367-5375, vol. 186, Publisher: American Association of Immunologists, Inc., Published in: www.jimmunol.org/cgi/doi/10.4049/jimmunol.1003438.
Yasufumi Goto et al., "Activation of toll-like receptors 2, 3, and 4 on human melanoma cells induces inflammatory factors", "Molecular Cancer Therapies", 2008, pp. 3642-3653, vol. 7, Publisher: American Association for Cancer Research, Published in: http://mct.aacrjournals.org/content/7/11/3642.
V. Jarrousse et al., "Toll-like receptors 2, 4 and 9 expression in cutaneous T-cell lymphoma (mycosis fungoides and Sezary syndrome)", "Europen Journal of Dermatology", 2006, pp. 636-741, vol. 16, No. 6, Publisher: John Libbey Eurotext, Published in: http://www.jle.com/en/revues/medecine/ejd/e-docs/00/04/28/35/article.phtml.
Geoffrey B. Johnson et al., "Receptor-Mediated Monitoring of Tissue Well-Being via Detection of Soluble Heparan Sulfate by Toll-Like Receptor 4", "Journal of Immunology", 2002, pp. 5233-5239, vol. 168, No. 10, Publisher: American Association of Immunologists, Inc., Published in: http://www.jimmunol.org/content/168/10/5233.

(Continued)

*Primary Examiner* — Peter J Reddig
(74) *Attorney, Agent, or Firm* — Eugene J. Molinelli; Buesse Wolter Sanks & Maire

(57) ABSTRACT

Toll-like receptors (TLR) are expressed by a variety of cancers, including melanoma and T-ALL. TLR signaling plays an important role in T cell malignancies and melanoma. The effects of stimulating or inhibiting the TLR/IL-1 receptor-associated kinases IRAK-1 and IRAK-4 in melanoma and T-ALL cells were evaluated. Pharmacological treatment with an IRAK-1,-4 inhibitor delays tumor growth and prolongs survival in vitro and in vivo, indicating that TLR signaling contributes to T-ALL and melanoma progression and interfering with this signaling is a novel therapeutic strategy to control T-ALL and melanoma proliferation.

11 Claims, 23 Drawing Sheets

(56) References Cited

OTHER PUBLICATIONS

Takamitsu Mizobe et al., "Constitutive association of MyD88 to IRAK in HTLV-Itransformed T cells", "Experimental Hematology", 2007, pp. 1812-1822, vol. 35, No. 12, Publisher: Elsevier, Published in: http://www.exphem.org/article/S0301-472X%2807%2900496-1/abstract.

Vassiliki Mollaki et al., "Polymorphisms and haplotypes in TLR9 and MYD88 are associated with the development of Hodgkins lymphoma: a canidate . . . ", "Journal of Human Genetics", 2009, pp. 655-659, vol. 54, Publisher: The Japan Society of Human Genetics, Published in: http://www.nature.com/jhg.

Monica Molteni et al., "Melanoma cell lines are responsive in vitro to lipopolysaccharide and express TLR-4", "Cancer Letters", 2006, pp. 75-83, vol. 235, No. 1, Publisher: Elsevier, Published in: http://www.sciencedirect.com/science/article/pii/S030438350500354X.

A. Nieters et al., "Gene polymorphisms in Toll-like receptors, interleukin-10, and interleukin-10 receptor alpha and lymphoma risk", "Genes and Immunity", 2006, pp. 615-624, vol. 7, No. 8, Publisher: Nature Publishing Group, Published in: http://www.nature.com/gene/journal/v7/n8/pdf/6364337a.pdf.

Mark P. Purdue et al., "A pooled investigation of Toll-like receptor gene variants and risk of non-Hodgkin lymphoma", "Carcinogenesis", 2009, pp. 275-281, vol. 30, No. 2, Publisher: Oxford University Press, Published in: http://carcin.oxfordjournals.org/content/30/2/275.full.

Melanie Saint-Jean et al., "TLR expression in human melanoma cells", "European Journal of Dermatology", 2011, pp. 899-905, vol. 21, No. 6, Publisher: John Libbey Eurotext, Published in: http://www.jle.com/en/revues/medecine/ejd/e-docs/00/04/70/C9/article.phtml.

Bruno Salaun et al., "Toll-like Receptor 3 Expressed by Melanoma Cells as a Target for Therapy?", "Clinical Cancer Research", 2007, pp. 4565-4574, vol. 13, Publisher: American Association for Cancer Research, Published in: http://clincancerres.aacrjournals.org/content/13/15/4565.full.pdf+html.

Thomas J. Smith et al., "Differential expression of Toll-like receptors in follicular lymphoma, diffuse large B-cell lymphoma and peripheral T-ce", "Experimental and Molecular Pathology", 2010, pp. 284-290, vol. 89, No. 3, Publisher: Elsevier, Published in: http://dx.doi.org/10.1016/j.yexmp.2010.08.003.

Vera Sobek et al., "Direct Toll-like receptor 2 mediated co-stimulation of T cells in the mouse system as a basis for chronic inflammatory . . . ", "Arthritis Research and Therapy", 2004, pp. R433-R446, vol. 6, No. 5, Publisher: BioMed Central Ltd, Published in: http://arthritis-research.com/content/6/5/R433.

Ratika Srivastava et al., "Augmentation of Therapeutic Responses in Melanoma by Inhibition of IRAK-1,-4", "Cancer Research", 2012, pp. 1-8, vol. 72, No. 23, Publisher: American Association for Cancer Research, Published in: http://cancerres.aacrjournals.org/lookup/doi/10.1158/0008-5472.CAN-12-0337.

Karen Rebecca Suchin et al., "Treatment of Stage IA Cutaneous T-Cell Lymphoma with Topical Application of the Immune Response Modifier Imiquimod", "Archives of Dermatology", 2002, pp. 1137-1139, vol. 138, Publisher: American Medical Association, Published in: http://archderm.jamanetwork.com/article.aspx?articleid=478946.

Christian Termeer et al., "Oligosaccharides of Hyaluronan Activate Dendritic Cells via Toll-like Receptor 4", "Journal of Experimental Medicine", 2002, pp. 99-111, vol. 195, No. 1, Publisher: Rockefeller University Press, Published in: http://www.jem.org/cgi/content/full/195/1/99.

Ramunas M. Vabulas et al., "Endocytosed HSP60s Use Toll-like Receptor 2 (TLR2) and TLR4 to Activate the Toll/Interleukin-1 Receptor Signaling . . . ", "Journal of Biological Chemistry", 2001, pp. 3133231339, vol. 276, No. 33, Publisher: The American Society for Biochemistry and Molecular Biology, Inc., Published in: http://www.jbc.org/content/276/33/31332.full.pdf+html?sid=6bf8df15-b1cc-4165-a450-2ea7ede0384c.

Robert P. A. Wallin et al., "Heat-shock proteins as activators of the innate immune system", "Trends in Immunology", 2002, pp. 130-135, vol. 23, No. 3, Publisher: Elsevier Science Ltd., Published in: http://www.sciencedirect.com/science/article/pii/S1471490601021688.

Zhulun Wang et al., "IRAK-4 Inhibitors for Inflammation", "Current Topics in Medicinal Chemistry", 2009, pp. 724-737, vol. 9, No. 8, Publisher: Bentham Science Publishers Ltd., Published in: http://www.benthamdirect.org/pages/article/1/3154854/irak-4-inhibitors-for-inflammation.html.

\* cited by examiner

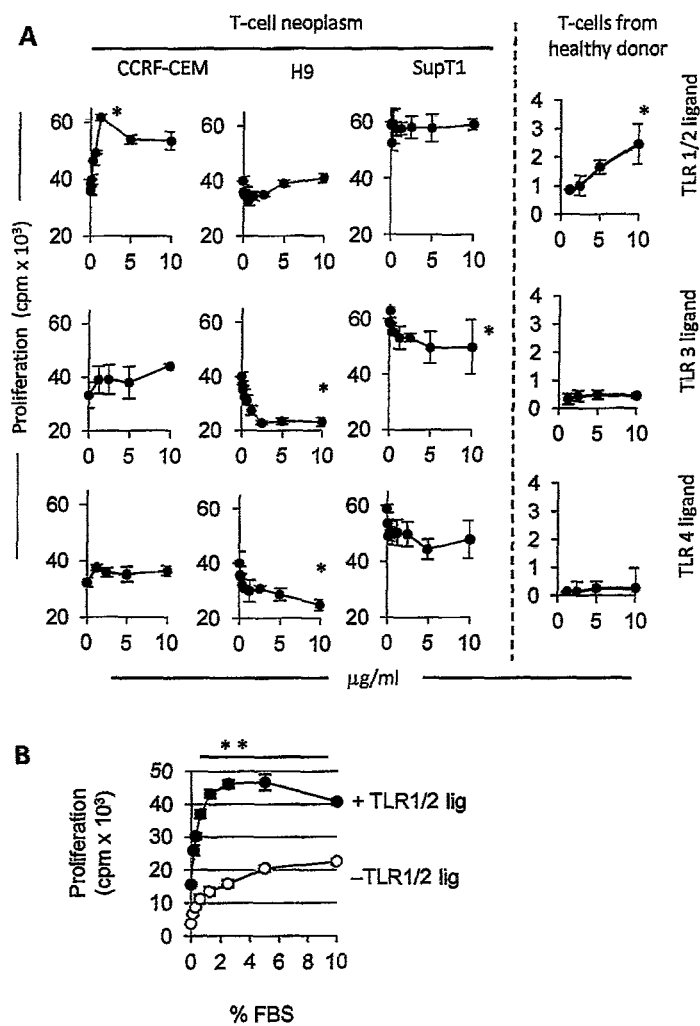
Figure 1. Proliferative effects of TLR agonists on T-cell neoplasms.

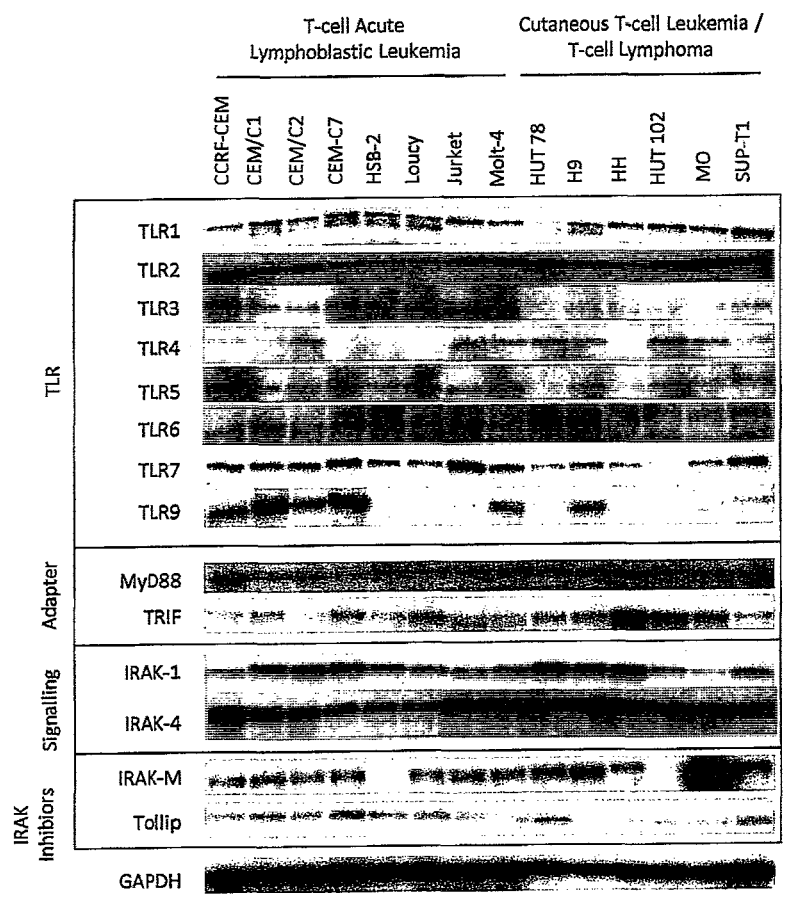
Figure 2. TLR and TLR-related expression profiles on T-cell neoplasms.

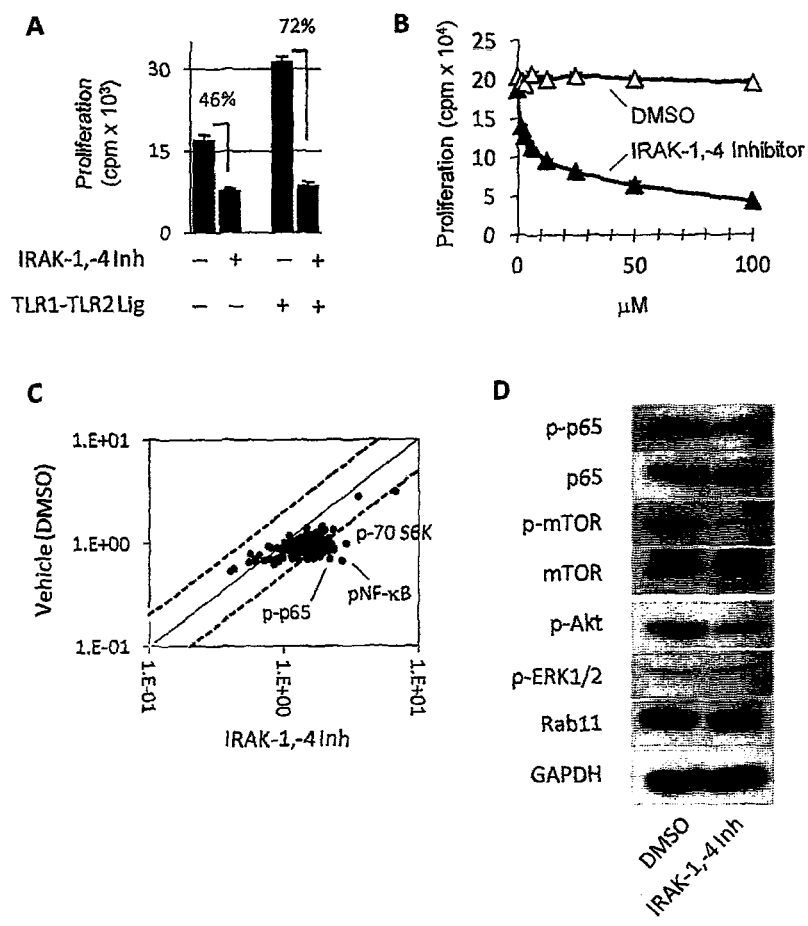
Figure 3. IRAK-1,-4 inhibition in T-ALL cells reduces cell survival and alters expression of cell survival-related proteins.

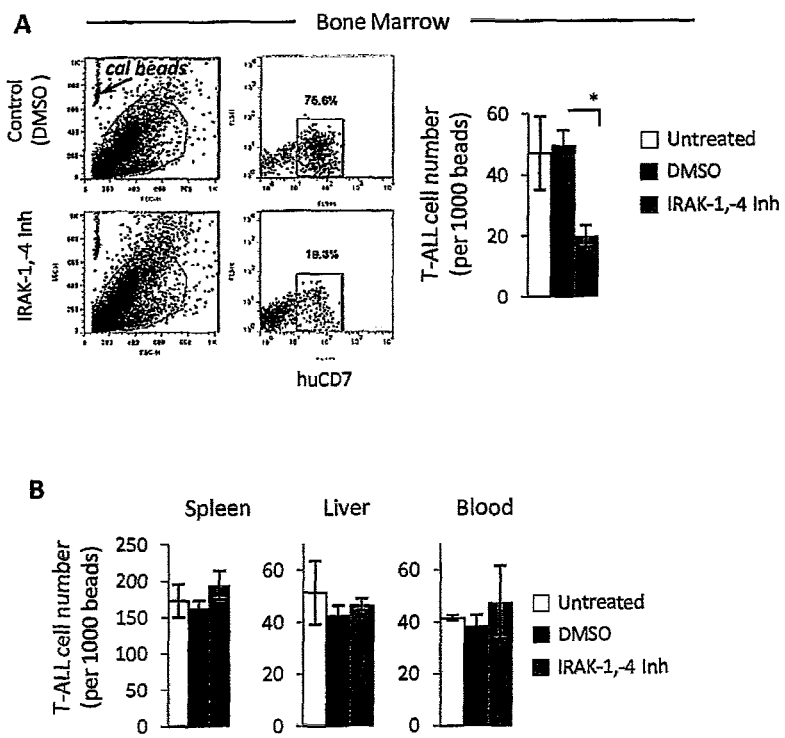
Figure 4. Treatment with IRAK-1,-4 inhibitors reduces T-ALL numbers *in vivo*.

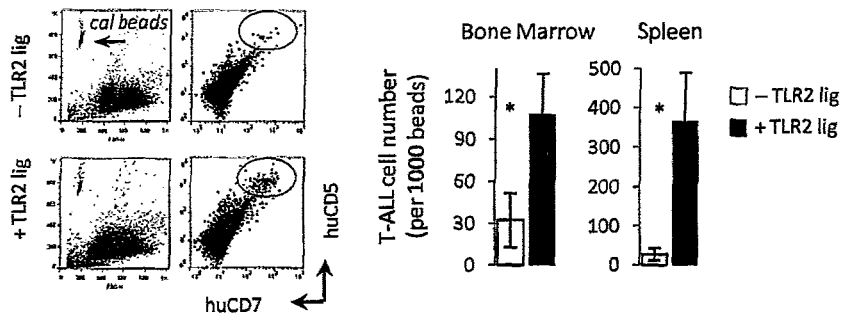
Figure 5. Injection with TLR1-TLR2 agonist enhances T-ALL expansion *in vivo*.

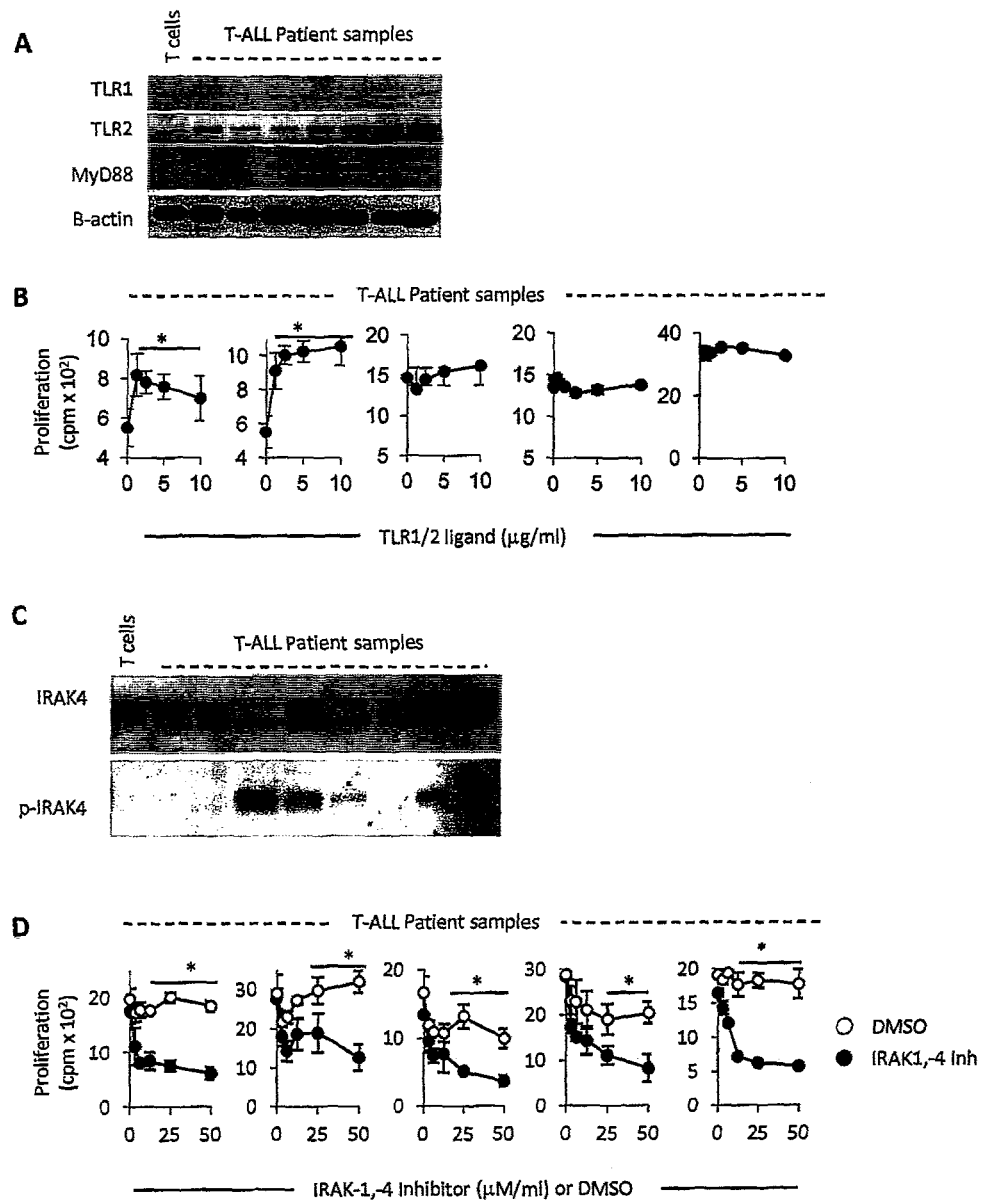
Figure 6. TLR1-TLR2 agonist augments patient T-ALL proliferation, whereas IRAK-1,-4 inhibition reduces T-ALL proliferation.

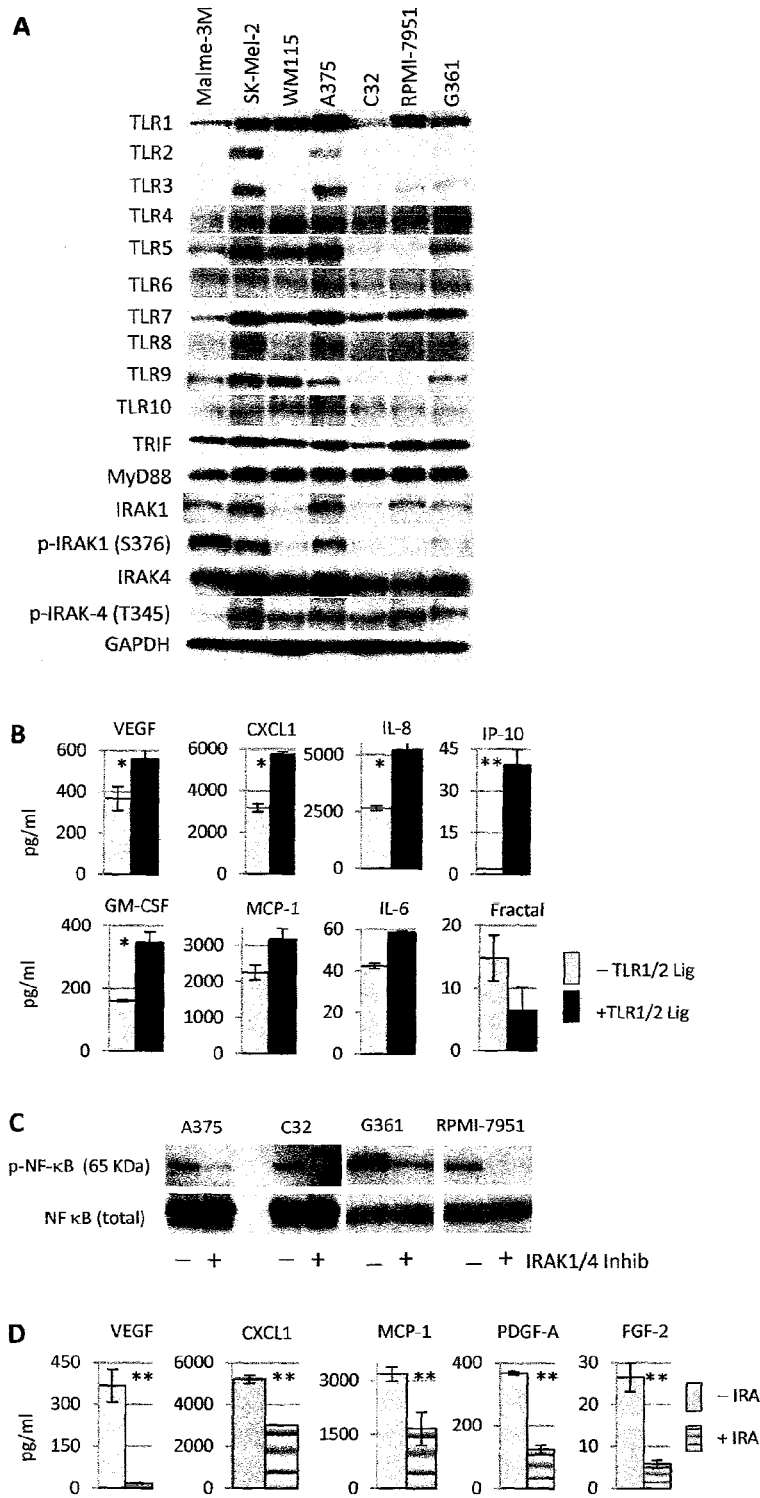
Figure 7. TLR and TLR signaling-related protein expression profiles on melanoma cell lines.

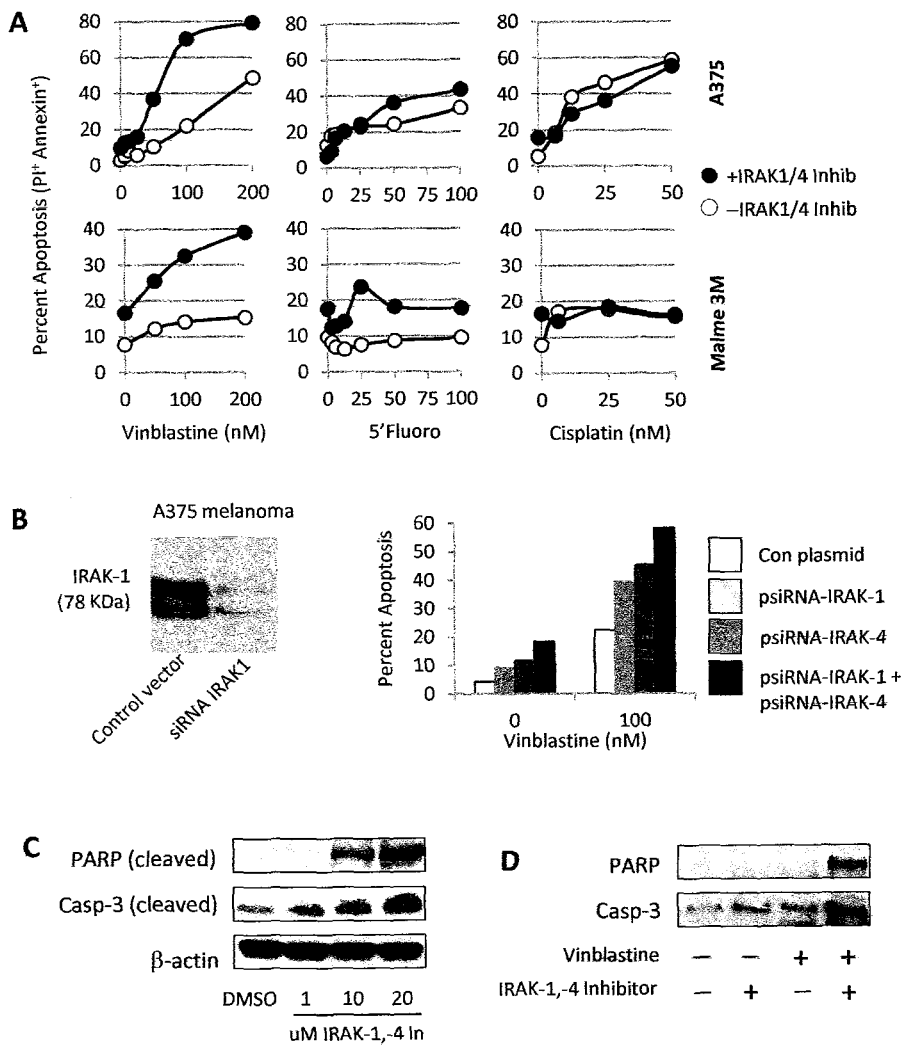
Figure 8. IRAK-1,-4 inhibition sensitizes melanoma cells to vinblastine-mediated cytotoxicity.

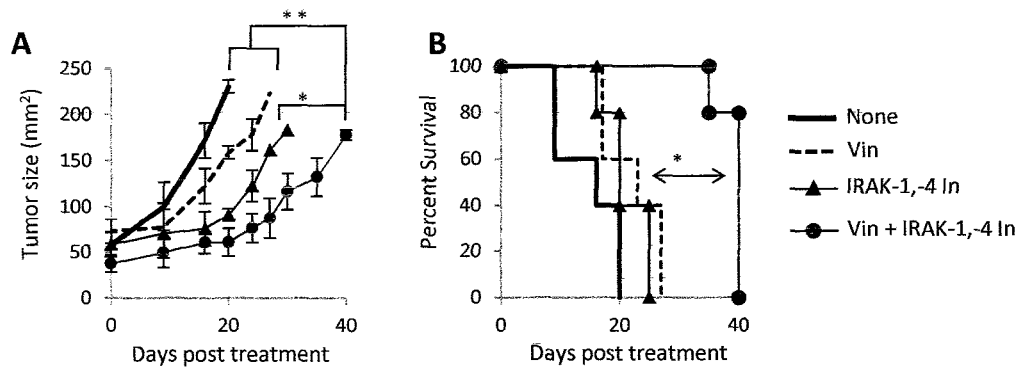
Figure 9. Treatment with IRAK-1,-4 inhibitor enhances the therapeutic effects of vinblastine in mice with an established human melanoma tumor.

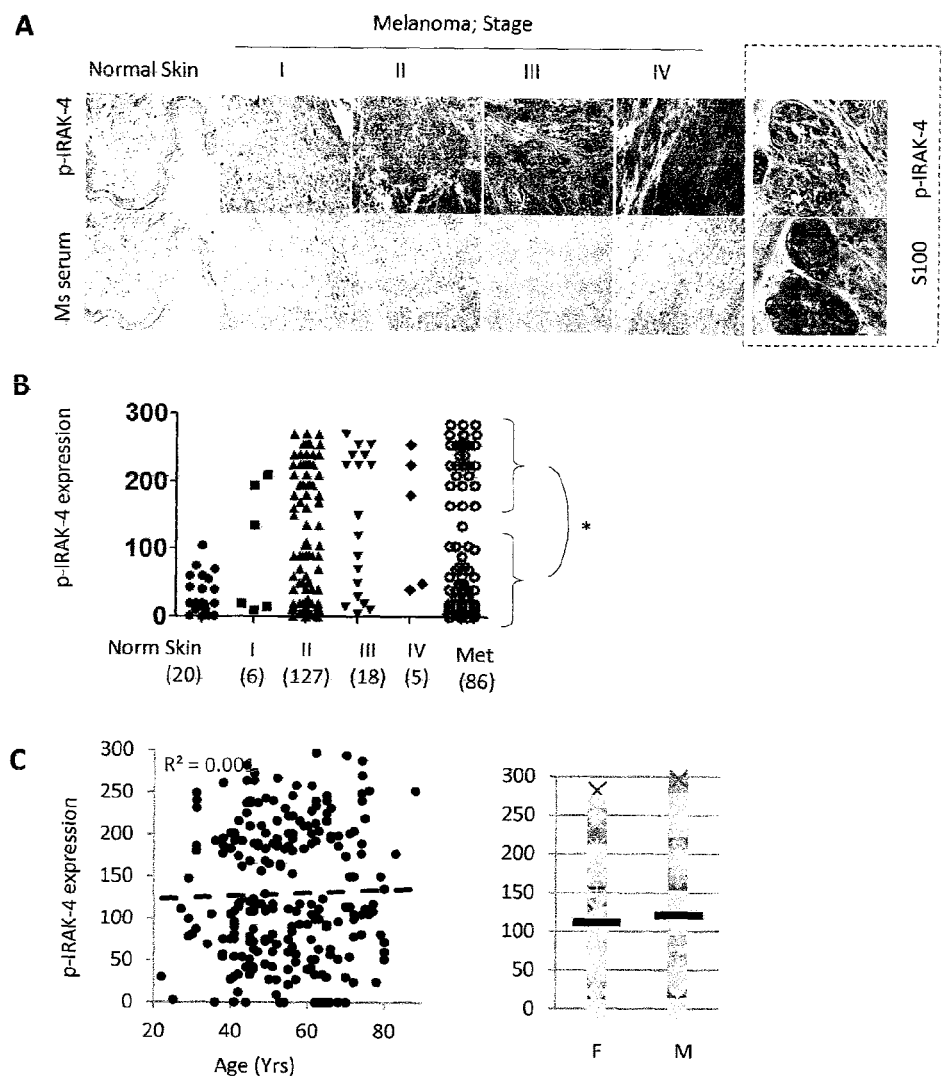
Figure 10. Expression of p-IRAK-4 in melanoma cells biopsy specimens.

FIG. 14A
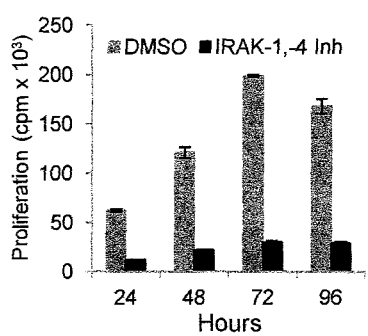
FIG. 14B
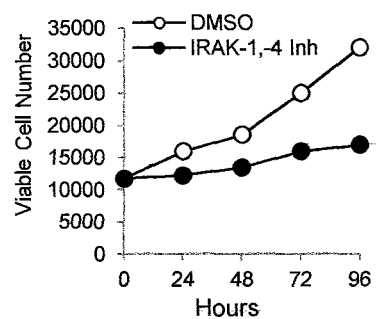
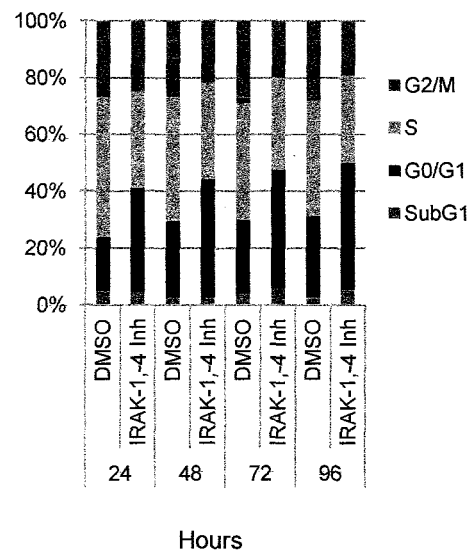
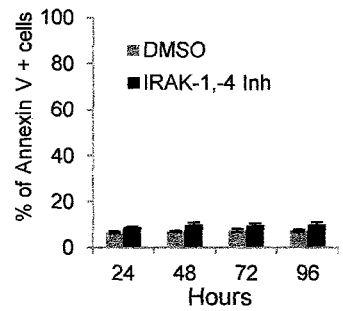
FIG. 14D
FIG. 14C

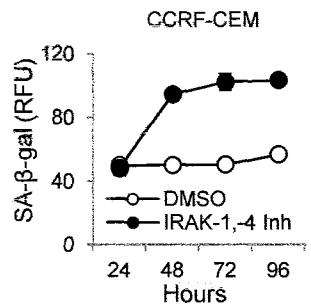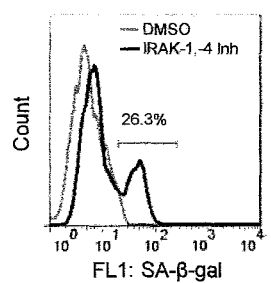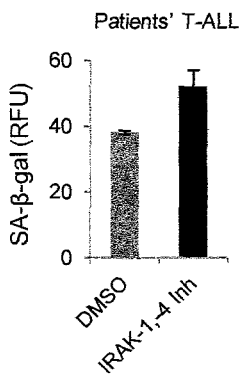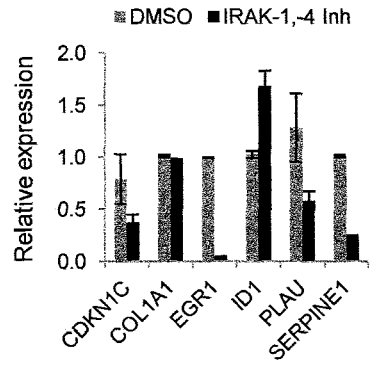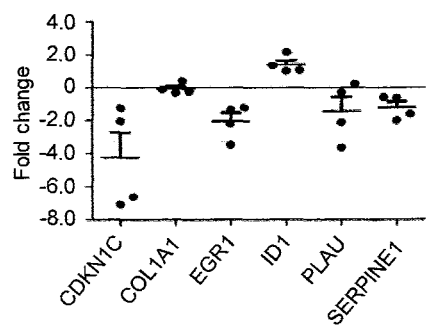
FIG. 15A
FIG. 15B
FIG. 15C
FIG. 15D
FIG. 15E ☐ G361-contorl plasmid
■ G361-pUNO-hIRAK-1

FIG. 21

| Gene | IRAK In vs DMSO | Vinblastine vs DMSO | Vin+IRAK In vs DMSO |
|---|---|---|---|
| BAK1 |  | 2.07 |  |
| BAX |  | 4.03 | 3.25 |
| BCL2L1 |  | 4.82 | 2.91 |
| BCL2L10 | -10.34 | -2.87 | -3.36 |
| BCL2L11 |  | 2.17 |  |
| BCLAF1 |  | 2.55 |  |
| BIK |  | 5.74 | 5.10 |
| BIRC1 | -3.81 | -3.01 |  |
| BIRC2 |  | 3.73 | 2.22 |
| BIRC3 |  | 4.50 | 3.20 |
| BIRC6 |  |  |  |
| BIRC8 |  |  | 2.55 |
| BNIP1 |  | 2.13 |  |
| BRAF | -2.20 |  | -2.45 |
| CARD6 |  | 3.14 | 2.13 |
| CASP5 | -10.34 | -9.38 | -10.56 |
| CASP9 | -3.23 | -2.11 | -2.57 |
| CD40 |  |  | -2.03 |
| CD40LG | -6.87 | -6.92 | -4.38 |
| CIDEA | -4.06 | -2.95 |  |
| DAPK1 |  | 2.38 |  |
| FADD |  | 2.83 | 2.04 |
| FAS |  | 9.85 | 7.84 |
| FASLG | 2.13 | 2.01 | 4.35 |
| GADD45A |  | 10.78 | 7.84 |
| IGF1R | -2.16 | -2.01 | -3.16 |
| LTA | -4.72 |  |  |
| MCL1 |  | 2.64 |  |
| NOL3 |  |  | -3.12 |
| PYCARD | -5.24 | -5.03 | -5.54 |
| TNF |  |  |  |
| TNFRSF10A |  | 4.11 | 2.68 |
| TNFRSF10B |  | 2.62 |  |
| TNFRSF11B | -3.34 |  |  |
| TNFSF8 | -2.19 |  |  |
| TNFSF10 | -3.18 | -2.23 | -2.30 |
| TP53 |  |  | -2.30 |
| TRADD |  |  | -2.01 |
| TRAF3 | -2.77 |  | -2.33 |

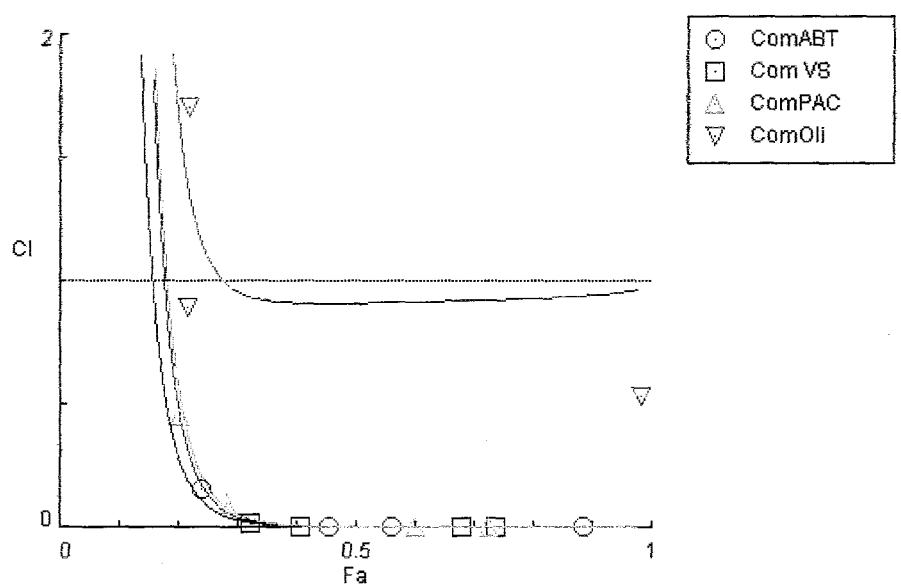
FIG. 23. IRAK-1,-4 inhibitor works in a synergy with other chemotherapeutics..

TOTAL AND PHOSPHORYLATED IL-1 RECEPTOR-ASSOCIATED KINASE-1 AND IL-1 RECEPTOR-ASSOCIATED KINASE-4 AS A BIOMARKER FOR CANCER PROGRESSION AND CHEMOTHERAPY RESISTANCE

CROSS-REFERENCE TO RELATED APPLICATIONS

This application claims the benefit of Provisional Application No. 61/614,196 filed Mar. 22, 2012, which is incorporated in its entirety.

REFERENCE TO SEQUENCE LISTING SUBMITTED VIA EFS-WEB

This application includes an electronically submitted sequence listing in .txt format. The .txt file contains a sequence listing entitled "ED2012072_P5209US01_20130601_ST25.txt" created on Jun. 1, 2013 and is 3,674 bytes in size. The sequence listing contained in this .txt file is part of the specification and is hereby incorporated by reference herein in its entirety.

STATEMENT OF GOVERNMENTAL INTEREST

This invention was made with Government support under Grant Number CA140917 awarded by the National Institutes of Health. The Government has certain rights in the invention.

BACKGROUND

Toll-like receptors are expressed by a variety of cancers, including T-cell ALL (T-ALL) and melanoma. Acute lymphoblastic leukemia (ALL) accounts for approximately 30% of cancers in children, making it the most common cancer in this age group (0-19 years) (1-3). T-ALL accounts for approximately 30% of all ALL cases. The use of conventional cancer therapies has resulted in a complete remission rate of approximately 75% in childhood T-ALL. In adults however, the 5-year survival rate is only 45-55%. Furthermore, T-ALL patients are also at increased risk of early recurrence and CNS relapse. The prognosis for relapsing patients is poor, with approximately 15% to 25% achieving stable remission after second-line treatment because of drug resistance and limited effective therapeutic options (2). Of note, unlike B-cell ALL, factors such as older age and a high white blood cell count are not reliable predictors in patients with T-ALL, rendering this patient population high-risk.

In addition to T-ALL, malignant melanoma is a life-threatening and aggressive type of skin cancer. Melanoma is the fifth most common cancer and is responsible for more than 75 percent of skin cancer-related deaths (39-40). The incidence of melanoma continues to rise world-wide but the development of new therapeutic agents has not kept up with the increased cancer occurrences. The median survival of patients with advanced disease is approximately 6 months and the survival rate at 5 years is 6% (39-40). Currently, there is no effective cure for patients with advanced melanoma. This is due in large part to their high resistance to chemotherapeutic drugs. Treatment failure is attributed to melanoma's resistance to all existing forms of cancer therapies.

Therefore, a need exists for the development of effective therapies and an ability to predict disease recurrence and therapy resistance in cancers such as T-ALL and melanoma.

SUMMARY OF THE INVENTION

It has been discovered that phosphorylated IRAK-4 was detected in T-ALL patient samples and phosphorylated IRAK-1 and phosphorylated IRAK-4 were detected in melanoma cell lines. Pharmacological inhibitors of IRAK-1,-4 reduced T-ALL in vitro and in vivo and alone, or in combination with a chemotherapeutic drug reduced melanoma expansion in vitro and in vivo thereby serving as a control for leukemia/lymphoma and melanoma progression.

A first set of embodiments is directed to methods of identifying a subject having cancer that expresses an active form of IRAK-1 or phosphorylated IRAK-1 or a variant thereof and/or active form of IRAK-4 or phosphorylated IRAK-4 or a variant thereof and administering to the subject, a therapeutically effective amount of an IRAK-1,-4 inhibitor in an amount that reduces or eliminates the cancer. Identifying a subject that will respond to treatment is the result of obtaining a biological sample of the cancer from the subject and determining if these cancer cells of the biological sample express an active form of IRAK-1 or phosphorylated form of IRAK-1 or a variant thereof and/or an active form of or phosphorylated form of IRAK-4 or a variant thereof. If the active form of IRAK-1 or phosphorylated form of IRAK-1 or a variant thereof and/or an active form of IRAK-4 or phosphorylated IRAK-4 or variant thereof is detected, then the subject will respond to treatment with an IRAK-1,-4 inhibitor and is treated. The subject may be human. Biological samples in certain embodiments include, but are not limited to, tumor biopsies, urine, blood, cerebrospinal fluid, sputum, serum, stool, or bone marrow. In certain embodiments, therapeutically effective amounts of the IRAK-1,-4 inhibitor range from about 1 mg/kg to 100 mg/kg per administration with as many administrations per day as are needed to achieve the desired result, depending upon the severity of the disease, the severity of illness in the patient, and for as long as needed.

In the above method, the cancer to be treated includes cancer cells selected from the group consisting of lung cancer, digestive and gastrointestinal cancer, gastrointestinal stromal and/or carcinoid tumors, colon cancer, rectal cancer, anal cancer, bile duct cancer, small intestine cancer, stomach (gastric) cancer, esophageal cancer, gall bladder cancer, liver cancer, pancreatic cancer, appendix cancer, breast cancer, ovarian cancer, renal cancer, cancer of the central nervous system, skin cancer, including but not limited to melanoma, lymphomas, leukemias, including but not limited to acute lymphoblastic anemias such as T-ALL and B-ALL, choriocarcinomas, head and neck cancers, osteogenic sarcomas, and blood cancer.

In methods of treatment, the IRAK-1,-4 inhibitor can be administered alone, or in combination with a chemotherapeutic drug, by any means that is shown to achieve the desired result, including orally, by injection (i.p., subcutaneous, i.v., intratumoral, peritumural etc.), parenterally, by inhalation, topically, rectally, nasally, buccally, vaginally, or via an implanted reservoir. IRAK-1,-4 inhibitor can be administered locally to the site of the cancer or tumor. Chemotherapeutic drugs are selected form the group consisting of vinblastine, 5'fluorouracil, and cisplatin. also It has also been found that IRAK-1,-4 inhibitors work in a synergistic fashion to reduce cell proliferation or induce apoptosis when combined with chemotherapeutic drugs such as vemurafenib, ipilimumab, and BMS-663513, ABT-737, PF-04929113, 17-AAG (Geldanamycin), 17-DMAG, BIIB021, BIIB021, SNX-2112, Vinflunine Tartrate, CYT997, Vincristine Sulfate, ABT-751, Docetaxel, Epothilone A, Paclitaxel (Taxol), Vinorelbine (Navelbine), Abiraterone Acetate, B16727, Eplerenone, KX2-391, and Irinotecan HCl Trihydrate. In some embodiments, the amount of chemotherapeutic drug is 3.7 mg/m$^2$ to about 100 mg/m$^2$.

Some embodiments are directed to pharmaceutical formulations comprising an IRAK-1,-4 inhibitor, alone, or in combination with one or more chemotherapeutic drugs as well as kits comprising them. In certain embodiments, a pharmaceutical formulation or kit comprising it, may comprise IRAK-1,-4 inhibitor, in an amount 1 mg/kg to about 100 mg/kg alone, or in combination with a chemotherapeutic drug. In some embodiments, the amount of chemotherapeutic drug is 3.7 mg/m$^2$ to about 100 mg/m$^2$. The amount of therapeutic agent depends on many factors including bioavailability, route of administration, the aggressiveness of the cancer, and whether the cancer is a tumor or circulating cancerous cells. The chemotherapeutic drug may be selected from the group consisting of vinblastine, 5'-fluorouracil, and cisplatin, vemurafenib, ipilimumab, and BMS-663513, ABT-737, PF-04929113, 17-AAG (Geldanamycin), 17-DMAG, BIIB021, BIIB021, SNX-2112, Vinflunine Tartrate, CYT997, Vincristine Sulfate, ABT-751, Docetaxel, Epothilone A, Paclitaxel (Taxol), inorelbine (Navelbine), Abiraterone Acetate, B16727, Eplerenone, KX2-391, and Irinotecan Hcl Trihydrate.

Certain embodiments of the present invention are directed to methods for determining if a subject with cancer, will respond to treatment (i.e., if the patient and the cancer will respond to treatment) with IRAK-1,-4 inhibitor. This is determined by obtaining a sample of the cancer cells from the subject, assaying the cells in the sample for the presence of an active form of or phosphorylated form of IRAK-1 or variant thereof or an active form of or phosphorylated form of IRAK-4, or variant thereof and if the cells have the active form of or phosphorylated form of IRAK-1 or IRAK-4, then determining that the subject will respond to treatment with the inhibitor or combinations. Then, a therapeutically effective amount of the IRAK-1,-4 inhibitor is administered to the subject. Preferably, the subject is human and the cancer is melanoma. The biological sample may be melanoma tissue.

Other embodiments are directed to methods comprising obtaining a biological sample of cells from a subject diagnosed with T-ALL and assaying the T-ALL cells in the sample for the expression of TLR1 and TLR2 and subsequently contacting the cells with a TLR-1 and TLR-2 agonist. If the TLR1 and TLR2 expression increases in response to administration of a TLR-1 and TLR2 agonist, then it is determined that T-ALL, will respond to treatment with an IRAK-1,-4 inhibitor.

Preferred methods are directed to identifying a patient having T-ALL and administering IRAK-1,-4 inhibitor to the patient in addition to identifying a patient having melanoma and administering IRAK-1,-4 inhibitor to the patient. In the context of the present invention, it is possible to identify a patient at risk of developing T-ALL or melanoma, by providing a test biological sample from a subject and a control biological sample from a healthy subject and determining the level of p-IRAK-1 or p-IRAK-4 in the test and control samples and if the expression of p-IRAK-1 or p-IRAK-4 in the test sample is significantly higher than the level of p-IRAK-1 or p-IRAK-4 expression in the control sample then it is determined that the individual is at risk for developing T-ALL or melanoma.

Finally, methods are contemplated for increasing the efficacy of a chemotherapeutic drug by administering an IRAK-1,-4 inhibitor in combination with the chemotherapeutic drug.

These and other features, aspects, and advantages of the present invention will become better understood with regard to the following description, appended claims, and accompanying figures.

BRIEF DESCRIPTION OF THE DRAWINGS

The following figures form part of the present specification and are included to further demonstrate certain embodiments of the present invention. The invention may be better understood by reference to one or more of these drawings in combination with the detailed description of specific embodiments presented herein.

FIG. 1. Proliferative effects of TLR agonists on T-cell neoplasms. (A) T-cell neoplasms and total T cells from a healthy donor were cultured in the presence of various concentrations of the indicated TLR ligands. Seventy-two hours later proliferation was determined by $^3$H-thymidine uptake (±SD). (B) CCRF-CEM cells were pre-treated or not with TLR1-2 ligand (Pam3CysK4; 2.5 ug/ml) for 48 hrs, washed and then cultured in the presence of varying concentrations of FBS. Forty-eight hours later proliferation (±SD) was determined by $^3$H-thymidine incorporation. ANOVA; **$P<0.001$, *$P<0.05$.

FIG. 2. TLR and TLR signaling related expression profiles on T-cell neoplasms. The expression levels of TLR1-TLR9 and various TLR-related proteins were examined by western blot in samples from non-TLR-treated T-cell neoplasms.

FIG. 3. IRAK-1,-4 inhibition in T-ALL cells reduces cell survival and alters expression of cell survival-related proteins. (A) CCRF-CEM cells were cultured in the presence of TLR1-TLR2 agonist (1 µg/ml), IRAK-1,-4 inhibitor (5 µM) or both. (B) CCRF-CEM cells were cultured in increasing concentrations of IRAK-1,-4 inhibitor or control (DMSO). (A and B) Forty-eight hours later, proliferation was measured by $^3$H-thymidine incorporation (±SD). (C, D) CCRF-CEM cells were treated with IRAK-1,-4 inhibitor (5 uM) or DMSO for 48 hours. Cells were then harvested and total cell lysates were analyzed by protein array or by Western blot for expression of the indicated proteins.

FIG. 4. Treatment with IRAK-1,-4 inhibitors reduces T-ALL numbers in vivo. CCRF-CEM cells were injected intravenously into NSG mice, followed by intraperitoneal injection with IRAK-1,-4 inhibitor (10 mg/kg) or control vehicle (DMSO) on days 3, 6 and 9. Numbers of T-ALL cells (CD7+) in bone marrow (A), spleen, liver, and blood (B) were determined on day 20 by flow cytometry. To compare T-ALL numbers between groups, 10 µl of calibration beads were added to 50 µl of blood (or marrow or spleen suspensions) and the flow cytometry instrument gates were set to count a constant number of beads. Representative dot plots from bone marrow are shown in A (left panel). ANOVA; *$P<0.05$.

FIG. 5. Injection with TLR1-TLR2 agonist enhances T-ALL expansion in vivo. CCRF-CEM cells were injected into NSG mice, followed by injection with TLR1-TLR2 agonists (2.5 µg) or PBS 48 hours later. Numbers of T-ALL cells (CD5+CD7+) in the bone marrow and spleen were determined 10 days later by flow cytometry as described in FIG. 4. ANOVA; *$P<0.05$.

FIG. 6. TLR1-TLR2 agonist augments patient T-ALL proliferation, whereas IRAK-1,-4 inhibition reduces T-ALL proliferation. (A and C) T-ALL cell lysate was collected from eight patient samples. TLR1, TLR2, MyD88, IRAK-4, p-IRAK-4 and p-actin expression levels were determined in cells by western blot. (B) T-ALL cells from patients expressing high levels of TLR1 and TLR2 were cultured in the presence of varying concentrations of TLR1-TLR2 agonists (Pam3CysK4). (D) Alternatively, T-ALL cells expressing high levels of p-IRAK-4 were cultured in the presence of different concentrations of IRAK-1,-4 inhibitor. Forty-eight hours later proliferation was measured by $^3$H-thymidine uptake (±SD). ANOVA; *P<0.05.

FIG. 7. TLR and TLR signaling-related protein expression profiles on melanoma cell lines. (A) The expression levels of TLR1-TLR10 and various TLR-related proteins were examined by Western blot in samples from human melanoma cell lines. (B) The TLR1-TLR2 ligand Pam$_3$CysK$_4$ was added to A375 cells for 48 hrs. Cytokine and chemokine production by was determined using a Milliplex cytokine/chemokine array. (C) IRAK-1,-4 inhibitor or vehicle alone (DMSO) was added to melanoma cells for 48 hrs. The level of phosphorylated and non-phosphorylated p65 subunit of NF-KB was determined by Western blot. (D) Cytokine and chemokine levels in the supernatant A375 cell culture were examined using a Milliplex cytokine/chemokine array 48 hours after adding IRAK-1,-4 inhibitor or DMSO. ANOVA; **P<0.001, *P<0.05.

FIG. 8. IRAK-1,-4 inhibition sensitized melanoma cells to vinblastine-mediated cytotoxicity. (A) A375 and Malme-3M melanoma cells were cultured with or without 2.5 μM of IRAK-1,-4 and in the presence varying concentrations of vinblastine, cisplatin or 5' Fluorouracil. Forty-eight hours later apoptosis was evaluated by staining cells with annexin-V and propidium iodide and analyzed by flow cytometry. (B) A375 cells were transfected via electroporation with siRNA-IRAK-1,-4. IRAK-1 protein levels were examined by Western blotting. A375-3control, A375-psiRNA-hIRAK-1, A375-psiRNA-hIRAK-4, or cells expressing both psiRNA-hIRAK-1 and -4 were cultured in the presence of vinblastine (100 nmol/L) for 48 hours and apoptosis was examined by flow cytometry. (C) A375 melanoma cells were cultured in the presence of vehicle alone (DMSO) or various concentrations of IRAK-1,-4. Forty-eight hours later cell lysates were used to analyze the expression of levels of cleaved PARP or caspase-3 by Western blots. (D) A375 melanoma cells were cultured with or without 2.5 μM of IRAK.-1,-4 and in the presence or absence of vinblastine for 48 hrs. PARP and caspase-3 levels were determined by Western blot.

FIG. 9. Treatment with IRAK-1,-4 inhibitor enhanced the therapeutic effects of vinblastine in mice with an established human melanoma tumor. (A-B) NSG mice (n=5) were injected subcutaneously with A375 melanoma cells. When tumors reached a size of approximately 50 mm$^2$ mice remained untreated or injected intraperitoneally with vinblastine mg/kg; administered every 2 days for 10 days), or peritumorally with IRAK-1,-4 inhibitor (35 mg/kg), or vinblastine plus IRAK.-1,-4 inhibitor. Tumor sizes were calculated by measuring perpendicular by longitudinal diameter; *, P<0.05. Mouse survival data were analyzed using the exact log-rank test;*, P<0.05, **P<0.001.

FIG. 10. Expression of p-IRAK-4 in melanoma cells biopsy specimens. (A) Biopsies obtained from melanoma patients at different clinical stages were stained for phosphorylated IRAK-4 and examined by immunohistochemistry. Mouse serum was used as a control to examine non-specific antibody staining. Representative staining from patients at different stages of cancer or normal skin are shown (×20 field sections). The number in parentheses below the clinical stage is the number of patient samples analyzed. (B and C) Quantification of p-IRAK-4 staining as a function of clinical stage, age, and gender. The dotted line in C (left panel) represents the trend line from all samples and the bar line in the right panel is the average p-IRAK-4 value generated from samples obtained from female and male patients.

FIG. 14. CCRF-CEM cells were treated with IRAK-1,-4 inhibitor (5 uM) or DMSO for 24, 48, 72, and 96 hours and then, proliferation (A), cell number (B), cell cycle (C), and apoptosis (D) were determined by $^3$H-thymidine incorporation, cell number counting, PI staining, and Annexin V staining respectively.

FIG. 15. IRAK-1,-4 inhibitor induces senescence-like phenotype in T-ALL. (A) Senescence-associated (SA)-β-gal activity was analyzed after CCRF-CEM cells were treated with IRAK-1,-4 inhibitor (5 μM) or DMSO for 24, 48, 72, and 96 hours. (B) Senescence cells (SA-β-gal positive cells) were analyzed by flow cytometry after CCRF-CEM cells were treated with IRAK-1,-4 inhibitor (5 μM) or DMSO for 48 hours. (C) SA-β-gal activity was analyzed in four T-ALL patient samples (#810, #819, #825, #828) from IRAK-1,-4 inhibitor- or DMSO-treated NSG mice. (D,E) Gene expression analysis of IRAK-1,-4 inhibitor (5 uM) or DMSO treated CCRF-CEM cells (D) and four T-ALL patient samples (#810, #819, #825, #828) from IRAK-1,-4 inhibitor- or DMSO-treated NSG mice (E) by RT-PCR.

FIG. 21. Apoptosis-related gene transcription array of A375 melanoma cells following IRAK inhibition with or without vinblastine. A375 cells were cultured in the presence or absence IRAK-1/-4 inhibitor (10 μM), vinblastine (100 nM), or both. RNA was collected and reverse transcribed 48 hours later and the levels of various apoptosis-related transcripts was determined using RT-PCR array (SuperArray).

FIG. 23. IRAK-1,-4 inhibitor works in synergy with other chemotherapeutic drugs. CCRF-CEM cells were cultured in the presence of various concentrations of IRAK-1,-4 inhibitor and chemotherapeutic drugs.

DETAILED DESCRIPTION

1. Definitions

Figure 11A:
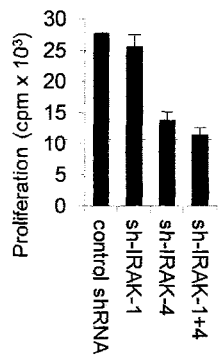
FIG. 11. IRAK-1,-4 inhibition in T-ALL cells reduces cell survival and alters expression of cell survival-related proteins. (A) CCRF-CEM cells were transfected with plasmids expressing control, IRAK-1 or/and IRAK-4 knockdown short hairpin RNAs. Positive transfected cells (GFP+ cells) were sorted by flow and proliferation was measured by $^3$H-thymidine incorporation (±SD). (B) T-ALL cell lysate was collected from eight patient samples as described in the Methods section. IRAK-4, p-IRAK-4 expression levels were determined in cells by western blot. (C) Patient T-ALL samples were cultured in increasing concentrations of IRAK-1,-4 inhibitor or control (DMSO). Seventy two hours later, proliferation was measured by $^3$H-thymidine incorporation (±SD). ANOVA; *P<0.05. (D) T-ALL cells expressing high levels of p-IRAK-4 were cultured in the presence of different concentrations of IRAK-1,-4 inhibitor. Seventy two hours later proliferation was measured by $^3$H-thymidine uptake (±SD).

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

IRAK-1, as used herein, means an interleukin-1 receptor-associated kinase 1, in the IRAK family, and is an enzyme that in humans is encoded by the IRAK1 gene. This gene encodes the interleukin-1 receptor-associated kinase 1, one of two putative serine/threonine kinases that become associated with the interleukin-1 receptor (IL1R) upon stimulation.

IRAK-4, as used herein means an interleukin-1 receptor-associated kinase 4, in the IRAK family, and is a protein kinase involved in signaling innate immune responses from Toll-like receptors. It also supports signaling from T-cell receptors.

IRAK-1,-4 inhibitor, as used herein, means a novel cell-permeable benzimidazole that is a potent inhibitor of interleukin-1 receptor-associated kinases 1 and 4 (IRAK-1,-4).

As used herein, "administering" a IRAK-1,-4 inhibitor e.g., IRAK-1,-4 alone or in combination with a chemotherapeutic drug, may be performed using any of the various methods of delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, introccularly, via local delivery, subcutaneously, intraadisposally, intraarticularly, intrathecally, into a cerebral ventricle, intraventricularly, intratumorally, into cerebral parenchyma or intraparenchymally or microinjection.

As used herein, the terms "animal," "patient," or "subject" include mammals, e.g., humans, dogs, cows, horses, kangaroos, pigs, sheep, goats, cats, mice, rabbits, rats, and transgenic non-human animals. The preferred animal, patient, or subject is a human.

The term, "kit" as used herein, means any manufacture (e.g., a package or container) comprising at least one reagent, e.g., an IRAK-1,-4 inhibitor and/or in combination with a chemotherapeutic drug. In certain embodiments, the manufacture may be promoted, distributed, or sold as a unit for performing the methods of the present invention.

A "subject" or "patient" is a mammal, typically a human, but optionally a mammalian animal of veterinary importance, including but not limited to horses, cattle, sheep, dogs, and cats.

A "therapeutic agent" is an inhibitor of interleukin-1 receptor-associated kinases 1 and 4 (IRAK-1,-4), or IRAK-1,-4 inhibitor, as herein described.

A "therapeutically effective amount" of a therapeutic agent is an amount that achieves the intended therapeutic effect of reducing or eliminating the cancerous cells, or tumor cells that express an active form or phosphorylated form of IRAK-1 or an active form or phosphorylated form of IRAK-4 in a subject thereby treating them. The full therapeutic effect does not necessarily occur by administration of one dose and may occur only after administration of a series of doses. Thus, a therapeutically effective amount may be administered in one or more administrations.

A "prophylactically effective amount" of a drug is an amount of a drug that, when administered to a subject, will have the intended prophylactic effect, e.g., preventing or delaying the onset (or reoccurrence) of the disease or symptoms, or reducing the likelihood of the onset (or reoccurrence) of the disease or symptoms. The full prophylactic effect does not necessarily occur by administration of one dose and may occur only after administration of a series of doses. Thus, a prophylactically effective amount may be administered in one or more administrations.

The term "significantly higher" as used herein, means levels of TRPV3 mRNA in a subject biopsy are at least a 15% increase over control levels.

The terms "treat" or "treatment" refer to both therapeutic treatment and prophylactic or preventative measures, wherein the object is to prevent or slow down (lessen) an undesired physiological change or disorder, such as the development, progression or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having cancer and those with cancer that expresses an active form or a phosphorylated form of IRAK-1 and/or an active form or a phosphorylated form of IRAK-4. "Treating" cancer in a patient refers to taking steps to obtain beneficial or desired results, including clinical results. For purposes of this invention, beneficial or desired clinical results include, but are not limited to alleviation or amelioration of one or more symptoms of the cancer; diminishing the extent of disease; delaying or slowing disease progression; amelioration and palliation or stabilization of the disease state.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; breast cancer; ovarian cancer; renal cancer (e.g., renal cell carcinoma); cancer of the central nervous system; skin cancer, including, but not limited to melanoma; lymphomas; leukemias; choriocarcinomas; head and neck cancers; osteogenic sarcomas; and blood cancers. As used herein, a "tumor" comprises one or more cancer cells.

The term "sample" as used herein includes any biological specimen obtained from a subject. Samples include, without limitation, a tissue sample (e.g., tumor tissue) such as a biopsy of a tumor, and cellular extracts thereof, whole blood, plasma, serum, red blood cells, white blood cells (e.g., peripheral blood mononuclear cells), saliva, urine, stool (i.e., feces), tears, nipple aspirate, lymph, fine needle aspirate, any other bodily fluid. In some embodiments, the sample is whole blood or a fractional component thereof such as plasma, serum, or a cell pellet. In certain embodiments, the sample is obtained by isolating circulating cells of a solid tumor from a whole blood cell pellet using any technique known in the art. As used herein, the term "circulating cancer cells" comprises cells that have either metastasized or micro metastasized from a solid tumor and includes circulating tumor cells, and cancer stem cells. In other embodiments, the sample is a formalin fixed paraffin embedded (FFPE) tumor tissue sample, e.g., from a solid tumor.

2. Overview

Toll-like receptors (TLR) are expressed by a variety of cancers, including melanoma and T-ALL, but their function contributions in cancer cells are uncertain. TLR signaling plays an important role in T cell malignancies and melanoma. The effects of stimulating or inhibiting the TLR/IL-1 receptor-associated kinases IRAK-1 and IRAK-4 in melanoma and T-ALL cells were evaluated. It has been discovered that phosphorylated IRAK-4 was detected in T-ALL patient samples and phosphorylated IRAK-1 and phosphorylated IRAK-4 were detected in melanoma cell lines. Pharmacological inhibitors of IRAK-1,-4 reduced T-ALL in vitro and in vivo and alone, or in combination with a chemotherapeutic drug reduced melanoma expansion in vitro and in vivo thereby serving as a control for leukemia/lymphoma and melanoma progression. Pharmacological treatment with an IRAK-1,-4 inhibitor delays tumor growth and prolongs survival in vitro and in vivo, indicating that TLR signaling contributes to T-ALL and melanoma progression and interfering with this signaling is a novel therapeutic strategy to control T-ALL and melanoma proliferation.

3. Background a. TLRs

Recent reports indicated that TLR signaling within non-immune cells, including several types of human cancers, can contribute to cancer progression (4-7). TLRs recognize infectious microorganisms as well as endogenous signals released by dying or stressed cells. The engagement of all known TLRs, except TLR3, initiates interleukin (IL)-1 receptor-associated kinase (IRAK) signaling (8-10). IL-1, IL-18, and IL-33 can also activate IRAK signaling. IRAK-4 kinase activity is regulated by autophosphorylation (Ser346, Thr342, and Thr345) (8-11), which in turn can activate IRAK-1. IRAK-1-4 activation results in the downstream activation of various kinases and transcription factors including JNK, AP-1, NF-KB, and p38 mitogen-activated protein kinase (MAPK), leading to the production of a mixture of chemokines and proinflammatory cytokines including TNF-alpha, IL-1, IL-6, and IL-8 (12). IRAK signaling can also induce the expression of several proteins involved in cell survival and division (13).

b. T-ALL

The prevalence of TLRs on mouse and human primary CD4 and CD8 T cells and the proliferative effects of TLR stimulation prompted the examination of the potential biological significance of these signals in T-cell neoplasms. The data presented here demonstrate that human T-cell lymphoma/leukemia cells, as well as cells from patients with T-ALL, express variable levels of TLRs and TLR-related proteins. Although most TLR ligands had no effect on T-cell survival or proliferation, other ligands, in particular the TLR1-TLR2 ligand, significantly enhanced proliferation/survival, whereas TLR3, TLR7, TLR8 and TLR9 ligands generally reduced proliferation. Furthermore, these studies support the contention that IRAK-1,-4 signaling in T-ALL cells plays a critical role in their proliferation/survival.

The studies presented examine the proliferative effects of various TLR ligands in several T-cell leukemia and lymphoma lines. However, other reports have suggested a link between TLR signaling and T-cell malignancies. For example, Mizobe and colleagues investigated whether MyD88-mediated signals contributed to NF-KB activation in HTLV-I-transformed adult T-cell leukemia/lymphoma (ATLL) T cells, and found constitutive association of MyD88 with IRAK-1 in several HTLV-I-transformed T-cell lines (14).

Notably, over-expressing a dominant negative form of MyD88 inhibited the constitutive activation of NF-KB, reduced proliferation and enhanced apoptosis. It is worth commenting that it was observed increased expression of constitutively activated IRAK in several T-ALL patient samples, suggesting that abnormal activation of the MyD88 (or downstream IRAK) signaling pathway may render cells more sensitive to TLR signaling. Alternatively, constitutive activation of IRAK may induce signaling even in the absence of TLR agonist and thereby contribute to disease progression.

Notch has been shown to play a key role in malignant transformation (15). It is estimated that 50% of T-ALL has activating mutations in Notch-1(15). Recent studies in macrophages demonstrate that Notch signaling can be activated by TLR stimulation (16). Furthermore, gamma-secretase inhibitors (GSI), which block the proteolytic activation of Notch (17-19), have been shown to target IL-1R-TRAF signaling, which is dependent on MyD88-IRAK signaling (20). It is tempting to speculate that in addition to blocking Notch signaling, GSis may also function, in part, by reducing MyD88-IRAK signaling. However, direct effects of GSis on TLR signaling in T-ALL cells have not been reported.

There was no clear correlation between TLR/TLR-signaling expression and TLR-induced proliferation in vitro, as not all cells that expressed TLRs responded to TLR agonists. Intracellular and extracellular TLR levels on T-cell neoplasms were examined by flow cytometry and similar expression patterns were found to those detected by western blot analysis. Therefore, differences in the cellular localization of receptors may not account for the variation in TLR sensitivity observed in vitro. On the other hand, defects in the TLR-signaling machinery may explain the lack of responses by cells. For example, changes in the expression levels of downstream adapter molecules (i.e. MyD88 and IRAKs) will inevitably impact the cell's ability to respond to TLR stimulation. Furthermore, because TLR signaling can be regulated by negative signals including surface receptors (e.g. TIR8/SIGIRR) and intracellular inhibitors (i.e. IRAK-M and Tollip), it is plausible that the expression levels of these molecules in malignant T cells may alter the outcome of TLR stimulation. Finally, whereas some TLR agonists induced proliferation, other ligands decreased proliferation. In general, it appeared that activation of signaling pathways that recognize nucleic acids (TLR3, TLR7, TLR8 and TLR9) was prone to induce apoptosis. These results could also caused by activation of other pattern recognition receptors such as NOD-like receptors, NOD, or other receptors on T-cell malignancies with different etiologies.

Whether TLR-MyD88-IRAK signaling in T-cell neoplasms contributes to disease progression in vivo, it has yet to be determined. Direct IRAK-1,-4 inhibition in T-ALL cells reduces proliferation and that TLR1-TLR2 stimulation enhances proliferation in vitro. Similarly, injecting leukemia-bearing mice with IRAK-1,-4 inhibitor reduced T-ALL expansion, whereas treatment with TLR1-TLR2 ligand enhanced T-ALL progression. However, it is important to point out that these effects might have also occurred indirectly by impacting endogenous mouse cells. Nevertheless, these data highlight the biological effects that altering IR.AK signaling in vivo has on T-ALL progression. The physiological significance of TLR signaling in T cell malignancies was also emphasized by Smith (21) and Jarrousse (22) who found TLR1, TLR2, TLR4, and TLR9 to be highly expressed in peripheral T-cell lymphoma, mycosis fungoides, and Sezary syndrome cutaneous lesions. Suchlin (23) reported that administration of a topical cream containing 5% of the TLR7 agonist Imiquimod successfully treated a stage IA cutaneous T-lymphoma. Several studies also highlight an association between TLRs and MyD88 gene polymorphisms and the risk for T-cell lymphoma (24-26). Furthermore, several studies in B-cell leukemia/lymphoma confirm the expression of functional TLRs on B-cell malignancies (27) and indicate that genetic differences in TLR/TLR-related genes may influence the development of hematological diseases including non-Hodgkin lymphoma (NHL) and Hodgkin lymphoma (H). Mollaki et al. demonstrated an association between TLR9/1237C and TLR9/2848A gene polymorphisms and the risk for HL (24). Purdue et al. found that two TLR10-TLR1-TLR6 variants in moderate linkage disequilibrium were significantly associated with NHL risk (25). Nieters et al. reported that the TLR2-16933TA variant was linked to a nearly 3-fold increased risk of follicular lymphoma, but a reduced risk of chronic lymphocytic leukemia (26). The TLR4 Asp299Gly variant was also associated with increased risk of HL and of mucosa-associated lymphoid tissue (MALT) lymphoma.

It is important to note that although TLRs are capable of sensing molecules from microbes, they also recognize a wide range of endogenous danger-associated molecular patterns (DAMPs), or so-called alarmins (28), released from dying or stressed cells. Among these alarmins are members of the heat-shock protein (HSP) family which have been shown to activate TLR2 and TLR4 (29-32). Interestingly, endogenous TLR9 and TLR2 agonists, released by damaged tissue in the synovium of rheumatoid arthritis, were reported to stimulate TLRs on T cells (33-34). The extracellular matrix proteins (ECM) such as oligosaccharides of hyaluronic acid (35) and heparan sulfate (36) have also been shown to behave as DAMPs. Recent studies also indicate that amyloid-a and in the serum as well as the high mobility group B1 can activate TLR2 and TLR4 signals (37-38). A role for these molecules in progression of T-cell neoplasms has yet to be clearly defined.

The physiological significance of TLR signaling in T cell malignancies has also been emphasized by Smith and Jarrousse (43), who found TLR1, TLR2, TLR4, and TLR9 to be highly expressed in peripheral T-cell lymphoma, mycosis fungoides, and Sézary syndrome cutaneous lesions. Suchlin (44) reported that administration of a topical cream containing 5% of the TLR7 agonist Imiquimod successfully treated a stage IA cutaneous T-lymphoma.

A connection between TLR signaling and cellular senescence has yet to be established. It is a first to demonstrate that inhibiting TLR signaling promotes cellular changes that resemble those seen in cellular senescence. Senescence is considered an alternative type of cell cycle arrest of high relevance for tumor suppression and chemotherapy response. In general, the Rb and p53 tumor suppressor pathways play important roles during cellular senescence and can be trigged by multiple mechanisms. It has been reported that hematopoietic stem cells (HSC) from mice repeatedly treated with very low doses of LPS show phenomena of aging, suggesting that activating TLR-4 signaling may contribute to cellular senescence. (45) Ingenuity pathways analysis, principal components factor analysis, and linkage analysis performed by Diego et al. in human lymphocytes suggest that TLR signaling may also play a role in lymphocyte senescence. (46). Another study by Lin, et al. showed that genetic deletion of TLR2 increased susceptibility to diethylnitrosamine (DEN) and was associated with a broad-spectrum reduction in the immune response to DEN-induced liver injury. (47). The defects in immune networks resulted in the suppressed p21- and p16/pRb-dependent senescence. Our studies demonstrate that inhibiting IRAK signaling induced cell cycle arrest and β-galactosidase expression in T-ALL cell lines and patient samples. Understanding how TLR signaling regulates cellular senescence in hematological malignancies is an ongoing effort in our group, with TLR's ability to alter NF-KB and mTOR activation as a possible mechanism.

It was reported that mTOR signaling-induced senescence occurs via mTORC1, while activation of mTORC2 prevents senescence in circulating angiogenic cells. (48-50). We found that IRAK-1,-4 inhibition dramatically reduced p-mTOR levels and induced senescence, implying a role for mTOR signaling through mTORC1 in T-ALL cells. It was also found that decreased NF-κB signaling activity in IRAK-1,-4 inhibitor-treated T-ALL cells, and a negative correlation between NF-κB and senescence has been recognized. (51-53). Six senescence-related genes were identified that were significantly up- or down-regulated after IRAK-1,-4 inhibition. Among them, EGR1 is particularly interesting, as some studies have shown that Egr1 is a tumor suppressor and that abrogation of Egr1 expression is accompanied by upregulation of cell senescence markers in breast cancer. (54-56). However, other studies indicate that expression of Egr1 in Egr1-null mouse embryo fibroblasts restores senescence and activation of EGR1 in mature megakaryocytes induces expression of senescence markers. (56-57).

CDKN1C has been shown to have a negative role in senescence in bladder cancer and hepatocellular carcinoma, (58-59)) suggesting an undescribed mechanism of CDKN1C in regulation of senescence in T-ALL. COL1A1, ID1, PLAU, and SERPINE1 are also involved in regulation of senescence in malignant tumors, (61-64) but additional studies are necessary to clarify the detailed mechanism by which IRAK signaling and the expression of these genes regulates senescence in T-ALL.

The biological importance of TLR-IRAK signaling in primary T cells is underscored. It is suggested that this signaling pathway may play an important role in the pathogenesis or progression of T-cell malignancies. Whereas TLR-IRAK activation might promote T-ALL progression, TLR signaling inhibition appears to skew cells towards a senescence-like phenotype. Identifying novel pathways that can slow the growth of chemotherapy-resistant cells in T-cell neoplasms or block molecular pathways that promote T-ALL growth would provide opportunities for the development of new targeted therapies for these malignancies.

c. Melanoma

Various TLRs have been shown to be expressed on various types of cancers including melanoma. The incidence of melanoma has been on the rise in the United States and worldwide over the last 30 years and has the fastest rising cancer incidence in the United States (50-52). Melanoma is the 5th/6th most common cancer in men and women, respectively (50-52). The median survival of patients with advanced disease is approximately 6 months and the survival rate at 5 years is 6% and 45% for Stage III patients (50-51). Treatment failure is largely attributed to melanoma's resistance to all existing forms of cancer therapies.

4. Summary of Experimental Results and Embodiments of the Invention

It has been discovered that IRAK-1,-4 inhibitor treatment had a dramatic effect on T-ALL expansion by mediating cell-cycle arrest and inducing a cellular senescence. The following is a summary of results of experiments relating to T-ALL described in the Examples of this application.

Some TLR ligands enhanced proliferation by 25% or greater, depending on the cell line, other TLR ligands reduced proliferation or had no effect on cell expansion.

Most T-ALL lines proliferated in response to TLR-1-TLR2 agonist.

Differences occur in the expression levels of TLRs and TLR-signaling proteins and the effects of TLR agonists are not solely dependent on TLR expression.

IRAK-1,-4 inhibition reduces T-ALL expansion and was effective at concentrations as low as 1.5 μM in CCRF-CEM cells.

IRAK-1,-4 signaling plays a critical role in cell survival through interplay with various key signaling molecules.

Treatment with IRAK-1,-4 inhibitors reduces CD7$^+$ T-ALL cells in vivo, i.e., in the bone marrow of mice.

Administration of TLR1-TLR2 ligand significantly augmented the T-ALL cell number in bone marrow and in spleen of mice.

T-ALL cells from leukemia patients express TLR1 and TLR2 and proliferate in response to TLR1-TLR2 agonist.

T-ALL cells from leukemia patients express phosphorylated IRAK-1,-4 and its inhibition reduces proliferation.

IRAK-1,-4 signaling inhibition in T-ALL cells modulates the expression of various prosurvival signaling pathways.

IRAK-1,-4 inhibitor reduces cell number by mediating cell cycle arrest, but not apoptosis.

IRAK-1,-4 inhibition induces a cellular senescence-like phenotype.

It has been discovered that IRAK-1,-4 inhibitor treatment had a dramatic effect on expansion and proliferation of melanoma cells and reduced cytokine and chemokine production molecules beneficial to cancer cell survival. The following is a summary of results of experiments relating to melanoma cells described in the Examples of this application.

TLR expression profiles vary on melanoma cell lines.

All melanoma cell lines expressed high levels of IRAK-4 whereas variable levels of IRAK-1 were detected in all melanoma cell lines.

The activated form of IRAK-1 was strongly expressed in Malme-3M, SK-MEL-2, and A375 cell lines and variable levels of p-IRAK-4 were detected in melanoma cells.

Constitutive expression of phosphorylated IRAK-1 and IRAK-4 occurs on human cutaneous melanoma cells.

Activation of IRAK-1,-4 signaling on melanoma cells in vivo contributes to cancer progression by inducing the expression of various chemokines and cytokines beneficial to cancer cell survival, division, and/or angiogenesis.

Inhibition of IRAK-1,-4 drastically reduced the production of several cytokines/chemokines.

IRAK inhibition sensitizes melanoma cells to certain chemotherapies in vitro and in vivo.

p-IRAK-4 is highly expressed in melanoma samples.

Methods of Treatment

Toll-like receptors (TLR) are expressed by a variety of cancers, including T-ALL and melanoma. TLR signaling within nonimmune cells, including several types of human cancers can contribute to cancer progression. In examining the TLR and TLR signaling-related protein expression profiles on various T-ALL and melanoma cell lines, it has been discovered that phosphorylated IRAK-4 was detected in T-ALL patient samples and phosphorylated IRAK-1 and phosphorylated IRAK-4 were detected in melanoma cell lines. Pharmacological inhibitors of IRAK-1,-4 reduced T-ALL in vitro and in vivo and alone, or in combination with a chemotherapeutic drug reduced melanoma expansion in vitro and in vivo thereby serving as a control for leukemia/lymphoma and melanoma progression. These results have strong therapeutic implications for treating cancer by administering an IRAK-1,-4 inhibitor to an afflicted subject.

Therefore, a first set of embodiments is directed to methods of identifying a subject having cancer that expresses an active form of IRAK-1 or phosphorylated IRAK-1 or a variant thereof and/or active form of IRAK-4 or phosphorylated IRAK-4 or a variant thereof and administering to the subject, a therapeutically effective amount of an IRAK-1,-4 inhibitor in an amount that reduces or eliminates the cancer. Identifying a subject that will respond to treatment is the result of obtaining a biological sample of the cancer from the subject and determining if these cancer cells of the biological sample express an active form of IRAK-1 or phosphorylated form of IRAK-1 or a variant thereof and/or an active form of or phosphorylated form of IRAK-4 or a variant thereof. If the active form of IRAK-1 or phosphorylated form of IRAK-1 or a variant thereof and/or an active form of IRAK-4 or phosphorylated IRAK-4 or variant thereof is detected, then the subject will respond to treatment with an IRAK-1,-4 inhibitor and is treated. The subject may be human. Biological samples in certain embodiments include, but are not limited to, tumor biopsies, urine, blood, cerebrospinal fluid, sputum, serum, stool, or bone marrow. In certain embodiments, therapeutically effective amounts of the IRAK-1,-4 inhibitor range from about 1 mg/kg to 100 mg/kg per administration with as many administrations per day as are needed to achieve the desired result, depending upon the severity of the disease, the severity of illness in the patient, and for as long as needed.

Cancers that express an active form of IRAK-1 or phosphorylated form of IRAK-1 or a variant thereof and/or an active form of IRAK-4 or phosphorylated form of IRAK-4 or variant thereof can be treated or prevented with the methods of the present invention. In these methods, the cancer to be treated includes cancer cells selected from the group consisting of lung cancer, digestive and gastrointestinal cancer, gastrointestinal stromal and/or carcinoid tumors, colon cancer, rectal cancer, anal cancer, bile duct cancer, small intestine cancer, stomach (gastric) cancer, esophageal cancer, gall bladder cancer, liver cancer, pancreatic cancer, appendix cancer, breast cancer, ovarian cancer, renal cancer, cancer of the central nervous system, skin cancer, including but not limited to melanoma, lymphomas, leukemias, including but not limited to acute lymphoblastic anemias such as T-ALL, choriocarcinomas, head and neck cancers, osteogenic sarcomas, and blood cancer.

In other methods of treatment, the IRAK-1,-4 inhibitor can be administered alone, or in combination with a chemotherapeutic drug, by any means that is shown to achieve the desired result, including orally, by injection (i.p., subcutaneous, i.v., intratumoral, peritumural etc.), parenterally, by inhalation, topically, rectally, nasally, buccally, vaginally, or via an implanted reservoir. IRAK-1,-4 inhibitor can be administered locally to the site of the cancer or tumor. Chemotherapeutic drugs are selected form the group consisting of vinblastine, 5'fluorouracil, and cisplatin, vemurafenib, ipilimumab, and BMS-663513. IRAK-1,-4 inhibitor has been shown to work in synergy with chemotherapeutic drugs such as ABT-737, vincristine and paclitaxel. In some embodiments, the amount of chemotherapeutic drug is 3.7 mg/m$^2$ to about 100 mg/m$^2$.

Some embodiments are directed to pharmaceutical formulations comprising an IRAK-1,-4 inhibitor, alone, or in combination with one or more chemotherapeutic drugs as well as kits comprising them. In certain embodiments, a pharmaceutical formulation or kit comprising it, may comprise IRAK-1,-4 inhibitor, in an amount 1 mg/kg to about 100 mg/kg alone, or in combination with a chemotherapeutic drug. In some embodiments, the amount of chemotherapeutic drug is 3.7 m g/m$^2$ to about 100 mg/m$^2$. The amount of therapeutic agent depends on many factors including bioavailability, route of administration, the aggressiveness of the cancer, and whether the cancer is a tumor or circulating cancerous cells. The chemotherapeutic drug may be selected from the group consisting of vinblastine, 5'-fluorouracil, and cisplatin, vemurafenib, ipilimumab, and BMS-663513, ABT-737, PF-04929113, 17-AAG (Geldanamycin), 17-DMAG, BIIB021, BIIB021, SNX-2112, Vinflunine Tartrate, CYT997, Vincristine Sulfate, ABT-751, Docetaxel, Epothilone A, Paclitaxel (Taxol), Vinorelbine (Navelbine), Abiraterone Acetate, B16727, Eplerenone, KX2-391, and Irinotecan Hcl Trihydrate.

Certain embodiments of the present invention are directed to methods for determining if a subject with cancer, will respond to treatment (i.e., if the patient and the cancer will respond to treatment) with IRAK-1,-4 inhibitor. This is determined by obtaining a sample of the cancer cells from the subject, assaying the cells in the sample for the presence of an active form of or phosphorylated form of IRAK-1 or variant thereof or an active form of or phosphorylated form of IRAK-4, or variant thereof and if the cells have the active form of or phosphorylated form of IRAK-1 or IRAK-4, then determining that the subject will respond to treatment with the inhibitor or combinations. Then, a therapeutically effective amount of the IRAK-1,-4 inhibitor is administered to the subject. Preferably, the subject is human and the cancer is melanoma. The biological sample may be melanoma tissue.

Other embodiments are directed to methods comprising obtaining a biological sample of cells from a subject diagnosed with T-ALL and assaying the T-ALL cells in the sample for the expression of TLR1 and TLR2 and subsequently contacting the cells with a TLR-1 and TLR-2 agonist. If the TLR1 and TLR2 expression increases in response to administration of a TLR-1 and TLR2 agonist, then it is determined that T-ALL, will respond to treatment with an IRAK-1,-4 inhibitor.

Preferred methods are directed to identifying a patient having T-ALL and administering IRAK-1,-4 inhibitor to the patient in addition to identifying a patient having melanoma and administering IRAK-1,-4 inhibitor to the patient. In the context of the present invention, it is possible to identify a patient at risk of developing T-ALL or melanoma, by providing a test biological sample from a subject and a control biological sample from a healthy subject and determining the level of p-IRAK-1 or p-IRAK-4 in the test and control samples and if the expression of p-IRAK-1 or p-IRAK-4 in the test sample is significantly higher than the level of p-IRAK-1 or p-IRAK-4 expression in the control sample then it is determined that the individual is at risk for developing T-ALL or melanoma.

Finally, methods are contemplated for increasing the efficacy of a chemotherapeutic drug by administering an IRAK-1,-4 inhibitor in combination with the chemotherapeutic drug. In a preferred embodiment, some chemotherapeutic drugs, such as, but not limited to, vinblastine, that have been deemed ineffective might be rendered therapeutically useful when combined with an IRAK-1,-4 inhibitor. Inhibiting the IRAK pathway e.g., in melanoma cells is important for their survival and indicates that interfering with this pathway can sensitize melanoma cells or at least function in concert with certain chemotherapies to enhance their toxic effects. It is contemplated to identify new chemotherapeutic agents that might be currently in use to treat other cancers (e.g., vemurafenib, ipilimumab, and BMS-663513, ABT-737, PF-04929113, 17-AAG (Geldanamycin), 17-DMAG, BIIB021, BIIB021, SNX-2112, Vinflunine Tartrate, CYT997, Vincristine Sulfate, ABT-751, Docetaxel, Epothilone A, Paclitaxel (Taxol), Vinorelbine (Navelbine), Abiraterone Acetate, B16727, Eplerenone, KX2-391, and Irinotecan Hcl Trihydrate) or other disorders but might be repurposed against melanoma, when joined with an IRAK-1,-4 inhibitor.

Administration of Therapeutic Agents

A "therapeutic agent" is an IRAK-1,-4 inhibitor. The therapeutically effective amount of a therapeutic agent depends upon a number of factors within the ordinarily skill of a physician, veterinarian, or researcher and will vary depending inter alia on the subject, the activity and bioavailability of the specific agent(s) employed, the age, body weight, general health, gender, and diet of the subject, severity of the disease, the time of administration, the route of administration, the rate of excretion, any drug combination, and the degree of expression or activity to be modulated. Contributing factors further include the type, location, aggressiveness and size of cancer, precancerous lesion or benign tumor. Some highly aggressive tumors may require higher therapeutic amounts, for example. The full therapeutic effect does not necessarily occur by administration of one dose and may occur only after administration of a series of doses. Thus, a therapeutically effective amount may be administered in one or more administrations, on the same day or on different days. Other inhibitors such as TAK-242 (restorvid) function upstream of IRAK-4 as well as a TAK-1 inhibitor called 5(Z)-7-oxozeaenol which functions downstream of IRAK-1. Both these compounds may have similar effects as to inhibiting IRAK-1,-4. New variations and derivatives of these compounds are being generated.

The therapeutic agent such IRAK-1,-4 inhibitor may be administered alone or in combination with a chemotherapeutic drug, including but not limited to vinblastine, 5'fluorouracil, and cisplatin, vemurafenib, ipilimumab, and BMS-663513, ABT-737, PF-04929113, 17-AAG (Geldanamycin), 17-DMAG, BIIB021, BIIB021, SNX-2112, Vinflunine Tartrate, CYT997, Vincristine Sulfate, ABT-751, Docetaxel, Epothilone A, Paclitaxel (Taxol), Vinorelbine (Navelbine), Abiraterone Acetate, B16727, Eplerenone, KX2-391, and Irinotecan HCl Trihydrate. These FDA approved chemotherapeutics shall be administered by one of skill in the art intravenously. Vinblastin may be administered to humans in therapeutically effective amounts ranging from about 3.7 mg/m$^2$-11.1 mg/m$^2$ not to exceed 18.5 mg/m$^2$. 5'fluorouracil may be administered to humans in therapeutically effective amounts ranging from 10 mg/kg to 15 mg/kg not to exceed 800 mg in a day. Cisplatin may be administered to humans in therapeutically effective amounts ranging from 20 mg/m$^2$ to 100 mg/m$^2$.

In the in vitro experiments described herein, amounts of IRAK-1,-4 inhibitor ranged from 1.5 μM-5 μM and were shown to have dramatic effects on T-ALL and melanoma expansion and proliferation. In the in vivo experiments using mice, IRAK-1,-4 was administered via i.p. injection at a dose of 10 mg/kg/. Based on these in vivo mice studies, IRAK-1,-4 can be administered to humans in therapeutically effective amounts ranging from about 1 mg/kg to about 100 mg/kg to treat cancer that expresses phosphorylated IRAK-1 or phosphorylated IRAK-4. A person of skill in the art can determine the therapeutically effective amount of IRAK-1,-4 inhibitor. Factors affecting the dose include the aggressiveness of the cancer, the route of administration, the frequency of administration, and the health of the subject.

Therapeutic agents may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraruterial, subcutaneous, intraperitoneal or intramuscular injection or infusion; or intracranial, e.g., intrathecal or intraventricular, administration. In some embodiments a slow release preparation comprising the therapeutic agents is administered. The therapeutic agents can be administered as a single treatment or in a series of treatments that continue as needed and for duration of time that causes one or more symptoms of the cancer to be reduced or ameliorated, or that achieves another desired effect.

The dose(s) vary, for example, depending upon the identity, size, and condition of the subject and severity of the disease, further depending upon the route by which the composition is to be administered and the desired effect. Appropriate doses of a therapeutic agent depend upon the potency with respect to the expression or activity to be modulated. The therapeutic agents can be administered to an animal (e.g., a human) at a relatively low dose at first, with the dose subsequently increased until an appropriate response is obtained.

A suitable subject is an individual or animal that has cancer such as T-ALL or melanoma, or a cancer that expresses an active form of or a phosphorylated form of IRAK-1 or an active form of or a phosphorylated form of IRAK-4. Administration of a therapeutic agent "in combination with" includes parallel administration of two agents to the patient over a period of time, co-administration (in which the agents are administered at approximately the same time, e.g., within about a few minutes to a few hours of one another), and co-formulation (in which the agents are combined or compounded into a single dosage form suitable for administration).

Pharmaceutical Compositions or Formulations

Some embodiments are directed to pharmaceutical formulations comprising an IRAK-1,-4 inhibitor, alone, or in combination with one or more chemotherapeutic drugs as well as kits comprising them. In certain embodiments, a pharmaceutical formulation may comprise IRAK-1,-4 inhibitor, in an amount 1 mg/kg to about 100 mg/kg alone, or in combination with a chemotherapeutic drug. In some embodiments, the amount of chemotherapeutic drug is administered intravenously and is preferably in the range 3.7 mg/m$^2$ to about 100 mg/m$^2$ The amount of therapeutic agent depends on many factors including bioavailability, route of administration, the aggressiveness of the cancer, and whether the cancer is a tumor or circulating cancerous cells. The chemotherapeutic drug may be selected from the group consisting of vinblastine, 5'-fluorouracil, and cisplatin. The therapeutic agents may be present in the pharmaceutical compositions in the form of salts of pharmaceutically acceptable acids or in the form of bases. The therapeutic agents may be present in amorphous form or in crystalline forms, including hydrates and solvates. Preferably, the pharmaceutical compositions comprise a therapeutically effective amount.

Pharmaceutically acceptable salts of the therapeutic agents described herein include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining pharmaceutically acceptable acid addition salts.

Salts derived from appropriate bases include alkali metal (e.g., sodium and potassium), alkaline earth metal (e.g., magnesium), ammonium and salts. This invention also envisions the qmitemization of any basic nitrogen-containing groups of the therapeutic agents disclosed herein. Water or oil-soluble or dispersible products may be obtained by such quaternization.

The therapeutic agents of the present invention are also meant to include all stereochemical forms of the therapeutic agents (i.e., the R and S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of the present invention are also meant to include compounds which differ only in the presence of one or more isotopically enriched atoms. For example, therapeutic agents in which one or more hydrogens are replaced by deuterium or tritium, or the replacement of one or more carbons by $^{13}$C- or $^{14}$C-enriched carbon are within the scope of this invention.

In a preferred embodiment, the therapeutic agents of the present invention are administered in a pharmaceutical composition that includes a pharmaceutically acceptable carrier, adjuvant, or vehicle. The term "pharmaceutically acceptable carrier, adjuvant, or vehicle" refers to a non-toxic carrier, adjuvant, or vehicle that does not destroy or significantly diminish the pharmacological activity of the therapeutic agent with which it is formulated. Pharmaceutically acceptable carriers, adjuvants or vehicles that may be used in the compositions of this invention encompass any of the standard pharmaceutically accepted liquid carriers, such as a phosphate-buffered saline solution, water, as well as emulsions such as an oil/water emulsion or a triglyceride emulsion. Solid carriers may include excipients such as starch, milk, sugar, certain types of clay, stearic acid, talc, gums, glycols, or other known excipients. Carriers may also include flavor and color additives or other ingredients. The formulations of the combination of the present invention may be prepared by methods well-known in the pharmaceutical arts and described herein. Exemplary acceptable pharmaceutical earners have been discussed above. An additional carrier, Cremophor™, may be useful, as it is a common vehicle for Taxol.

The pharmaceutical compositions of the present invention are preferably administered orally, preferably as solid compositions. However, the pharmaceutical compositions may be administered intravenously, parenterally, by inhalation spray, topically, rectally, nasally, buccally, vaginally or via an implanted reservoir or prior to, at the same time as, or after intravenous administration of a chemotherapeutic drug. Sterile injectable forms of the pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

The pharmaceutical compositions employed in the present invention may be orally administered in any orally acceptable dosage form, including, but not limited to, solid forms such as capsules and tablets. In the case of tablets for oral use, carriers commonly used include microcrystalline cellulose, lactose and corn starch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

The pharmaceutical compositions employed in the present invention may also be administered by nasal aerosol or inhalation. Such pharmaceutical compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Should topical administration be desired, it can be accomplished using any method commonly known to those skilled in the art and includes but is not limited to incorporation of the pharmaceutical composition into creams, ointments, or transdermal patches.

The passage of agents through the blood-brain barrier to the brain can be enhanced by improving either the permeability of the agent itself or by altering the characteristics of the blood-brain barrier. Thus, the passage of the agent can be facilitated by increasing its lipid solubility through chemical modification, and/or by its coupling to a cationic carrier. The passage of the agent can also be facilitated by its covalent coupling to a peptide vector capable of transporting the agent through the blood-brain barrier. Peptide transport vectors known as blood-brain barrier permeabilizer compounds are disclosed in U.S. Pat. No. 5,268,164. Site specific macromolecules with lipophilic characteristics useful for delivery to the brain are disclosed in U.S. Pat. No. 6,005,004.

Solutions or suspensions used for parenteral, intradermal, or subcutaneous application can comprise the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. Pharmaceutical compositions suitable for injection comprise sterile aqueous solutions (where water soluble) or dispersions and sterile powders for the extemporaneous preparation of sterile injectable solutions or dispersions. For intravenous administration, suitable carriers comprise physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the selected particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, isotonic agents are included in the composition, for example, sugars, polyalcohols such as manitol, sorbitol, or sodium chloride. Prolonged absorption of an injectable composition can be achieved by including in the composition an agent that delays absorption, for example, aluminum monostearate or gelatin.

Sterile injectable solutions can be prepared by incorporating the active compound in the specified amount in an appropriate solvent with one or a combination of ingredients enumerated above, as needed, followed by filtered sterilization. Generally, dispersions are prepared by incorporating the active compound into a sterile vehicle that contains a basic dispersion medium and other ingredients selected from those enumerated above or others known in the art. In the case of sterile powders for the preparation of sterile injectable solutions, the methods of preparation comprise vacuum drying and freeze-drying which yields a powder of the active ingredient plus any additional desired ingredient from a previously sterile-filtered solution thereof.

Oral compositions generally comprise an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be comprised as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Ptimogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and comprise, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

A. T-ALL Cell Lines

Example 1

Materials and Methods for T-ALL Cell Lines

CCRF-CEM, CEM/C1, CEM/C2, CEM-C7, Jurkat, Loucy, Molt-4, HSB-2, SUP-T1, Hut 78, HH, Hut 102, MO, and H9 T-leukemia and T-lymphoma cell lines were purchased from the American Type Culture Collection (Manassas, Va., USA). All of the cell lines were initially expanded and cryopreserved within one month of receipt. Cells were typically used for 6 months at which time a fresh vial of cryopreserved cells was used. Total T cells from healthy donors were isolated via negative selection followed by positive selection using a CD3+ selection kit (Invitrogen, Carlsbad, Calif.). T cells were isolated from patients with T-ALL bone marrow or peripheral blood samples containing more than 70% leukemia cells using a CD2+ isolation kit (STEMCELL Technologies, Vancouver, Canada). All tissues were collected under institutional IRB-approved protocols and all participants gave written informed assent/consent. For in vitro experiments, T-ALL cells were cultured in AIM-V medium supplemented with 20% human AB serum in the presence of recombinant human stem cell factor (50 ng/mL; Amgen, Thousand Oaks, Calif.), insulin (20 nM; Sigma-Aldrich, St Louis, Mo., USA) and IL-7 (50 ng/mL; R&D Systems, Minneapolis, Minn., USA). In other experiments, protein lysate was collected using the Full Moon Biosystems (Sunnyvale, Calif., USA) buffer prior to protein examination by western blot or protein array.

Proliferation, Cell Number and Apoptosis Assays

Cells were cultured in a 96-well plate (Corning Costar, Corning, N.Y., USA) with various concentrations of TLR ligands 1-9, starting at 10 µg/ml, in a final volume of 200 ul. TLR ligands were diluted 2-fold. Cell lines ($25-40 \times 10^3$/well) were cultured for 54 hours, whereas fresh patient-derived T-ALL cells ($200 \times 10^3$/well) were cultured for 30 hours prior to adding [$^3$H]-thymidine for 18 hours. After this time point, cells were harvested with a Packard Filter-Mate-96 cell harvester (Perkin Elmer, Waltham, Mass., USA) and counted on Packard Top Count-NXT (Perkin Elmer, Waltham, Mass., USA). Results were expressed as average counts per minute (cpm). In some experiments CCRF-CEM cells were pre-treated with TLR1-TLR2 ligand (Pam3CysK4; 2.5 ug/ml) for 48 hrs, washed, and then cultured in the presence of varying concentrations of FBS. Forty-eight hours later, proliferation (±SD) was determined by $^3$H-thymidine incorporation. Alternatively, apoptosis was measured by flow cytometry after staining cells with Annexin-V (BD Pharmingen, San Diego, Calif., USA) and propidium iodide (Sigma). Cell number was counted under microscopy by staining cells with trypan blue.

Cell Cycle Analysis

Control and treated cells were collected, fixed and stained with propidium iodide (100 µg/mL) in PBS containing sodium citrate (1 mg/mL), Triton-X-100 (0.1%), and RNAse (20 µg/mL) for 30 min. Data were acquired on a BD FACScan flow cytometer using CellQuest software (BD Immunocytometry Systems, San Jose, Calif.) and analyzed by using FlowJo software (Tree Star, Inc., Ashland, Oreg.).

Cellular Senescence Assay

Analysis of senescence-associated β-galactosidase (SA-β-gal) activity was performed using the 96-Well Cellular Senescence Assay Kit (Cell Biolabs, San Diego, Calif.) as per the manufacturer's protocol. In brief, cells were washed with PBS, lysed with cell lysis buffer, and incubated at 37° C. with SA-β-gal substrate for 1 hour. A quantitative Cellular Senescence Assay Kit (SA-β-gal, Fluorometric) (Cell Biolabs, San Diego, Calif.) was used for more quantitative measurement of SA-β-gal activity by flow cytometry. Briefly, control and treated CCRF-CEM cells were incubated with 1× cell pretreatment solution in culture medium for 2 hrs, and the fluorogenic substrate was then directly added into the culture. After 4 hrs, the cells were washed and analyzed by flow cytometry.

Real-Time PCR and qPCR Array

Real-Time PCR and qPCR array assays were previously described.[9] The primers used for qPCR are listed in Table 2 (SEQ ID NOS: 1-16).

TLR Agonists and IRAK Inhibitor

The following TLR ligands were purchased from Invivogen (San Diego, Calif., USA): tripalmitoyl-S-(bis(palmitoyloxy)propyl)-Cys-Ser-(Lys)3-Lys (TLR1-2); Poly I:C (TLR3); ultrapure *S. Minnesota* Lipopolysaccharide (TLR4); *S. typhimurium* flagellin (TLR5); FSL-1 (TLR2/6); Imiquimod (TLR7); ssRNA40/Lyovec (TLR8); CpG-ODN 2006 (TLR9). In some experiments we used the IRAK-1,-4 inhibitor, which is a cell-permeable benzimidazole compound that selectively inhibits IRAK-1 and -4 and exhibits little to no activity against a panel of 27 other kinases (EMD Millipore, Darmstadt, Germany).

Mice

CCRF-CEM ($2 \times 10^6$) cells were injected intravenously (i.v.) into female NOD.Cg-Prkdc$^{scid}$ Il2rg$^{tm1\,WJl}$/SzJ IL2RG (NSG) mice (Jackson Laboratories, Bar Harbor, Me.). Use of mice was approved by the Institutional Animal Care and Use Committee. In some experiments mice were injected i.v. with TLR1-TLR2 ligand (2.5 µg) two days after injecting cells. In other experiments mice were injected intraperitoneally (i.p.) with IRAK-1,-4 inhibitor (10 mg/kg) 3, 6, and 9 days (CCRF-CEM cells) or 7, 10, and 13 days (patient T-ALL cells) after detecting CD7$^+$ T-ALL cells in circulation. The numbers of T-ALL cells in the bone marrow, spleen, liver, and in circulation were determined by staining cells with anti-human CD7 and/or CD5. To compare T-ALL numbers between groups, 10 µl of calibration microbeads (BD Pharmingen) were added to 50 µl of blood (or marrow or spleen suspensions) and the flow cytometry instrument gates were set to count a constant number of beads.

Western Blot and Protein Array

Total cell extracts were prepared from neoplastic T-cell lines or cells from patients with T-ALL. Proteins (20 µg/lane from cell lines and ~60 µg/lane from T-ALL patient) were resolved in Tris-glycine sodium dodecyl sulfate (SDS) gels and transferred to polyvinylidene difluoride membranes. The membrane was blocked for four hours with 5% milk in PBS and 0.05% Tween-20, followed by incubation with antibodies against TLR1 (N-23), phosphorylated p-IRAK-1 (Ser 376), total IRAK-1 (H-273) (Santa Cruz Biotech, Santa Cruz, Calif., USA); TLR2, TLR4, TLR7, TLR9, TRIF, IRAK-M, IRAK-4, Tollip, p65, p-p65, p-mTOR, mTOR, p-Akt, p-ERK1/2 Rab11, GAPDH (14C10) (Cell signaling, Danvers, Mass., USA); TLR3/CD283, TLR5 (IMGENEX, San Diego, Calif., USA); TLR6 (3D10H11), TLR8 (44C143), MyD88 (Abcam, Cambridge, Mass., USA) overnight at 4° C. and, subsequently, incubation with horseradish peroxidase-conjugated secondary antibody, and detection using enhanced chemiluminescence (ECL; Amersham Pharmacia Biotech). We also used a protein array from Full Moon Biosystems (Sunnyvale, Calif., USA). For these experiments, purified T-ALL cells were incubated for 48 hours in the presence of IRAK-1,-4 inhibitor (5 µM) or an equal volume of vehicle (DMSO). Then, total protein was extracted, and the levels of various proteins were measured according to the manufacturer's protocol.

Example 2

T-Cell Leukemia/Lymphoma Proliferative Response to TLR Agonists

Recent studies demonstrate that TLR engagement on primary T cells influences proliferation and survival (4-12). However, neither the TLR expression profile nor the physiological importance of TLR signals in human T-cell neoplasms has been fully characterized. The proliferative effects of TLR1-TLR9 agonists were examined in nine human T-cell leukemia and five T-lymphoma lines. Malignant T-cell lines responded differently to specific TLR ligands. For example, whereas the pre-T-ALL cell line CCRF-CEM proliferated in response to Pam3CysK4 (TLR1-2 agonist; 1.2 µg/ml), this ligand had no effect on proliferation of H9 T-lymphoma or SupT1 T-lymphoblastic leukemia at the different concentrations tested (FIG. 1A). In contrast, the TLR3 ligand poly I:C significantly reduced the proliferation of H9 cells while displaying a moderate anti-proliferative effect on SuptT1 cells at concentrations above 0.6 µg/ml. However, TLR3 agonist did not affect CCRF-CEM proliferation. The TLR4 ligand LPS also reduced expansion of H9 cells and SupT1 proliferation, but had no effect on CCRF-CEM cells. In T cells from healthy donors, TLR1-TLR2 stimulation enhanced proliferation when provided together with T cell receptor stimulation. Neither TLR4 nor TLR3 agonists had an effect on T-cell expansion. In primary T cells the effects of TLR agonists were dependent on concomitant TCR stimulation (FIG. 1A), indicating that the stimulatory/inhibitory effects of TLR agonists on T cells occur on activated/proliferating T cells.

The proliferative effects of other TLR agonists on various T-cell leukemia and lymphoma lines are shown in Table 1. These data highlight that, whereas some TLR ligands enhanced proliferation by 25% or greater (represented by a "+" symbol), depending on the cell line, other TLR ligands reduced proliferation ("−") or had no effect on cell expansion ("∘"). Most T-ALL lines proliferated in response to the TLR1-TLR2 agonist, whereas T-cell lymphoma/leukemia cells did not appear responsive to this agonist.

Figure 16A:
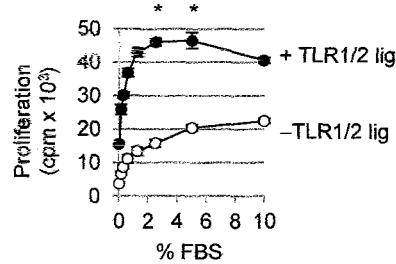
FIG. 16. (A) The expression levels of TLR1-TLR9 and various TLR-related proteins were examined by western blot in samples from non-TLR-treated T-cell neoplasms. These data are representative of three experiments each demonstrating similar expression profiles (B) CCRF-CEM cells were pre-treated or not with TLR1-2 ligand (Pam$_3$CysK$_4$; 2.5 μg/ml) for 48 hrs, washed and then cultured in the presence of varying concentrations of FBS. Seventy-two hours later proliferation was determined by 3H-thymidine incorporation. (C) T-ALL cell lysate was collected form eight patient samples. TLR1, TLR2, MyD88, and β-actin expression levels were determined in cells by western blot.

Previous reports demonstrate that activation of TLR1-TLR2-MyD88 signals in primary T cells can enhance cell survival despite exposure to various types of cellular stresses including serum deprivation (12, 19-24). In agreement with these reports, the proliferative effects of TLR1-TLR2 agonists on CCRF-CEM T-ALL cells were more pronounced when cells were cultured in decreasing serum levels (FIG. 1B, FIG. 16A). Altogether, these data indicate that depending on the TLR agonist and the malignant T cell on which TLR signals occurs, TLR ligands can alter proliferation and survival.

Example 3

TLR Expression Profiles in Different Malignant T-Cell Subsets

Figure 16B:
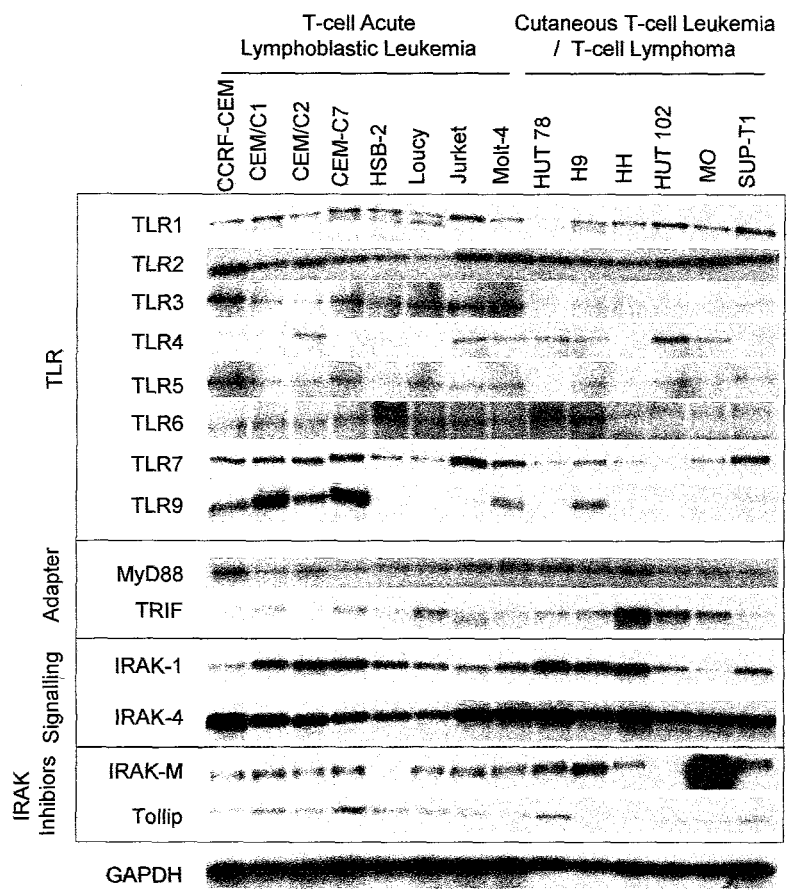

Expression of TLR1-TLR9 on T-cell leukemia and lymphoma lines were assessed by western blot. With the exception of Hut 78, all T-cell neoplasms expressed variable levels of TLR1 (FIG. 2, FIG. 16B). Similarly, most cell lines expressed detectable but variable levels of TLR2. TLR3 was absent or weakly expressed in T-lymphoma lines but present on lymphoblastic leukemia cell lines. TLR4 expression was most prominent on Hut 102 T-lymphoma cells while Jurkat, Molt4, Hut 78, MO, and H9 expressed moderate levels. TLR5 was weakly expressed by all cell lines except Hut 78 and HH, which did not express TLR5. TLR6 was most highly expressed on HSB2, Hut 78, and H9 and weakly expressed by the other cell lines. All cell lines except Hut 102 expressed variable levels of TLR7. The pre-T-ALL lines CCRF-CEM, CEM/C1, CEM/C2, and CEM/C7 expressed high levels of TLR9, whereas Molt-4 and H9 showed moderate levels of TLR9.

Expression levels of TLR adapter molecules and key signaling intermediates were also examined. The adapter molecule MyD88 was variably expressed in the different cell lines (FIG. 2). The T-cell lymphoma cell lines HH and Hut 102, as well as the 'hairy' cell leukemia MO, expressed the highest levels of TRIP. Hut 102 and MO showed reduced proliferation in response to TLR3 and TLR4 ligands, both of which transduce signals via TRIP. All cell lines expressed variable levels of IRAK-1, with CCRF-CEM, Jurkat, and MO expressing the lowest levels. IRAK-4 was also expressed at variable levels in all of the different cell lines.

Given the importance of IRAK in TLR signaling, the protein levels of the IRAK-1 inhibitors IRAK-M and Tollip were further investigated. IRAK-M expression is generally restricted to monocytes/macrophages and negatively regulates TLR signaling by preventing the dissociation of IRAK from MyD88 and thus thwarting the formation of IRAK-TRAF6 complexes. Whereas IRAK-M was highly expressed in MO cells, it was not detected in Hut 102 or HSB2 cells. The remainder of the cell lines expressed moderate but varying degrees of IRAK-M. Tollip negatively regulates TLR signals by associating directly with the TIR domain of TLRs, thus preventing activation of signals downstream of MyD88. With the exception of the H9 and HH cell lines, all cell lines expressed weak but highly variable levels of Tollip. These data emphasize the differences in the expression levels of TLRs and TLR-signaling proteins. These results also highlight that the effects of TLR agonists are not solely dependent on TLR expression, as not all cells that expressed TLRs responded to TLR agonists.

Example 4

IRAK-1,-4 Inhibition Reduces T-ALL Expansion

The effects of TLR1-TLR2 require the activation of IRAK.-1 and -4. To confirm that the effects of Pam3CysK4 occurred in a TLR-IRAK-dependent pathway in T-ALL cells, CCRF-CEM cells were treated with IRAK-1,-4 inhibitor in the presence or absence of the TLR1-TLR2 agonist. IRAK-1,-4 inhibition reduced the proliferation of TLR1-TLR2-stimulated cells by 72% (FIG. 3A). IRAK-1,-4 inhibition reduced proliferation in a concentration-dependent manner and was effective at concentrations as low as 1.5 µM (FIG. 3B). To examine in greater detail the anti-proliferative effects of IRAK-1,-4 inhibition, CCRR-CEM T-ALL cells were cultured in the presence of titrating concentrations of IRAK-1,-4 inhibitor, specifically in the absence of TLR agonists. The effects of IRAK-1 or IRAK-4 inhibition were further confirmed by knocking down IRAK-1 and/or IRAK-4 expression through transient transfection of plasmids expressing IRAK-1- and/or IRAK-4 targeting short hairpin RNAs (FIG. 11A). Knocking down IRAK-4 inhibited cell proliferation whereas knocking down IRAK-1 did not alter proliferation. In addition to blocking TLR-mediated signals, IRAK inhibition interfered with signals that contributed to cell expansion and/or survival. More specifically, TLR agonist stimulates T-ALL proliferation in a TLR-MyD88-IRAK signaling in T-ALL cells contribute to cell expansion and/or survival in a TLR agonist-independent mechanism.

Example 5

IRAK Signaling Modulates the Expression of Apoptosis-Related Molecules in T-ALL Cells To gain a better mechanistic understanding of how IRAK inhibition impacts cell cycle and cell survival, protein expression profiles between IRAK-1,-4 inhibitor-treated and control (DMSO treated) T-ALL cells were compared using an antibody array to compare the expression profile of apoptosis-related proteins between T-ALL cells treated with vehicle (DMSO) and IRAK-1,-4 inhibitor. The scatter plot in FIG. 3C shows the changes in protein levels between treated cells. The protein names are listed in Table 3. In particular, reduced expression levels of phosphorylated p65 (p-p65), p-NF-Kβ, pBcl-$X_L$, and p-70S6K were detected following IRAK.-1,-4 inhibition. (FIG. 3C). The changes in p-p65 were confirmed by western blot (FIG. 3D). Phosphorylated-p65 levels were decreased nearly four-fold following IRAK-1,-4 inhibition (FIG. 3D). IRAK-1,-4 inhibition also noticeably reduced the expression levels of p-mTOR and p-Akt (FIG. 3D). The expression levels of p-mTOR were reduced approximately six-fold and p-AKT nearly five-fold. (FIG. 3D). These results are consistent with recent reports demonstrating that TLR1-TLR2 signaling in primary T cells is linked to increased levels of p-Akt and p-mTOR (10,16). In contrast, IRAK inhibition did not alter p-ERK1/2 levels. (FIG. 3D).

Figure 13:
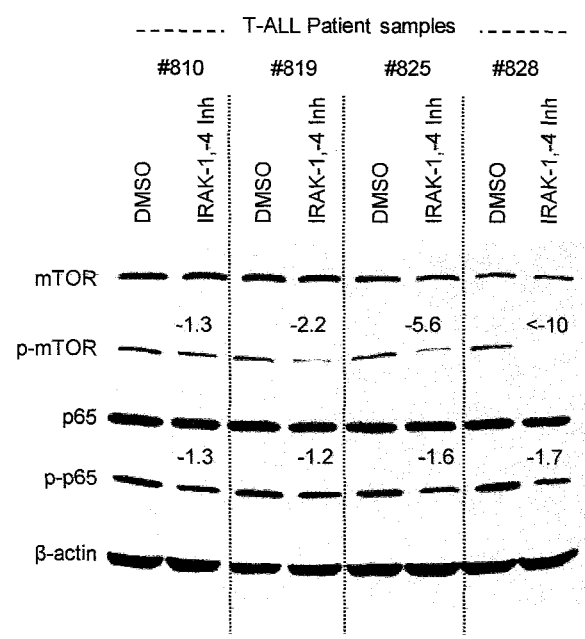
FIG. 13. CCRF-CEM cells were treated with IRAK-1,-4 inhibitor (5 uM) or DMSO for 48 hours. Four T-ALL patient samples from IRAK-1,-4 inhibitor- or DMSO-treated NSG mice were blotted by indicated proteins.

The levels of p-mTOR and p-p65 were also examined in patient T-ALL samples obtained from mice treated with IRAK-1,-4 inhibitor or DMSO. IRAK inhibitor reduced p-mTOR levels between 2.2 and 10-fold in patient samples #819, #825, and #828 (FIG. 13). Patient cells that demonstrated the greatest reduction in p-mTOR levels (#819, #825, and #828) also expressed the highest p-IRAK-4 levels, suggesting that these cells were highly sensitive to IRAK-1,-4 inhibitor further establishing a link between IRAK and m-TOR signaling.

Figure 11B:
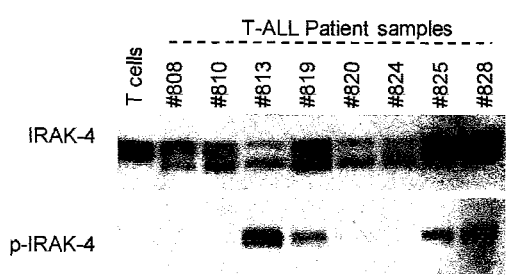
Figure 11C:
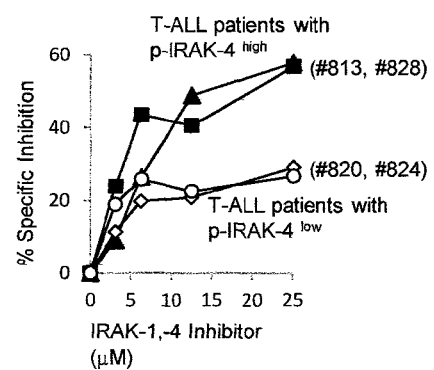
Figure 11D:
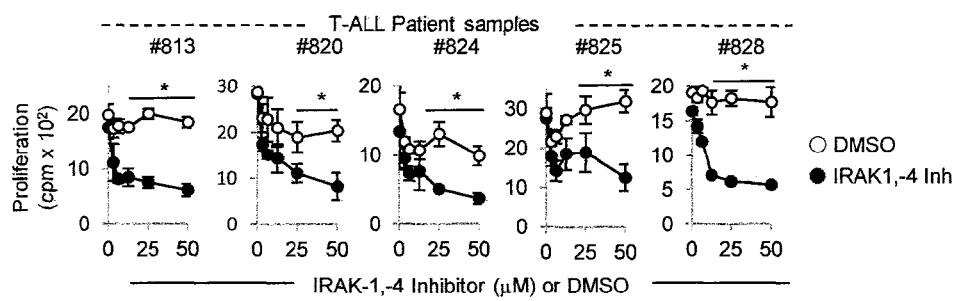

In contrast, patient sample #810 expressed the lowest (barely detectable) (FIG. 11B) levels of p-IRAK-4 and did not show changes in p-mTOR levels following treatment with IRAK-1,-4 inhibitor in vivo. p-p65 levels were also reduced nearly two-fold in patient samples #825 and #828. (FIG. 11C). Altogether these data that IRAK-1,-4 signaling plays a critical role in maintaining cell numbers through interplay with various key signaling molecules associated with cell survival/proliferation and protein synthesis. (FIGS. 11A-11D). Furthermore, these data highlight some similarities between T-ALL cells treated with IRAK-1,04 inhibitor in vitro and T-ALL cells obtained from treated mice, suggesting that similar molecular mechanisms are activated in T-ALL cells in vitro and in vivo.

Example 6

Treatment with IRAK-1,-4 Inhibitors Reduces T-ALL Numbers In Vivo

Figure 17:
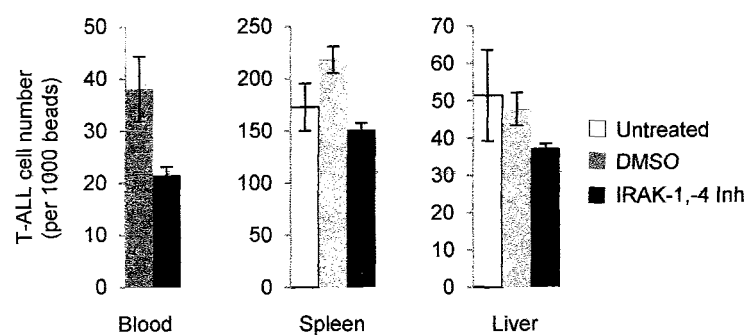
FIG. 17. CCRF-CEM cells were injected intravenously into NSG mice, followed by intraperitoneal injection with IRAK-1,-4 inhibitor (10 mg/Kg) or control vehicle (DMSO) on days 3, 6 and 9. Numbers of T-ALL cells (CD7$^+$) in spleen, liver, and blood were determined on day 20 by flow cytometry as described in FIG. 1. T-ALL cell numbers were not examined in circulation in untreated mice.

The therapeutic efficacy of IRAK-1,-4 inhibitor was examined in mice with T-ALL. NSG mice were injected (i.v.) with the human T-ALL cell line CCRF-CEM. Mice were intraperitoneally (i.p.) injected with IRAK-1,-4 inhibitor 3, 6, and 9 days after T-ALL cells were detected in the circulation. The number of T-ALL cells in various tissues was determined four days after the final IRAK-1,-4 inhibitor injection by staining cells with human-specific anti-CD7 antibodies and analyzing by flow cytometry. The number of T-ALL cells was counted after normalization to calibration beads. As demonstrated in FIG. 4A, and FIG. 17, IRAK-1,-4 inhibitors significantly reduced the number of CD7+ T-ALL cells in the bone marrow and in circulation, as compared with mice treated with DMSO vehicle or untreated mice (p<0.05; ANOVA). However, T-ALL cell numbers in the spleen and liver were only moderately reduced in IRAK-1,-4 inhibitor-treated mice (FIG. 17) and in the spleen, liver, and in circulation were similar between untreated, DMSO-treated and IRAK-1,-4 inhibitor-treated mice (FIG. 4B).

Example 7

TLR1-TLR2 Agonist Augments T-ALL Expansion In Vivo

The physiological significance of activating TLR-IRAK signaling and T-ALL expansion was examined in vivo. NSG mice harboring CCRF-CEM cells were injected with either TLR1-TLR2 ligand or PBS. One week later the numbers of CD5+CD7+ T-ALL cells in bone marrow and spleen were determined by flow cytometry (FIG. 5, left). To normalize the T-ALL cell count between mice, an equal volume of calibration beads was added to blood samples and the instrument gates were set to count a constant number of beads. The administration of TLR1-TLR2 ligand significantly augmented the T-ALL cell number in the bone marrow and in the spleen as compared with cell numbers in control mice (FIG. 5, right; p<0.05). The results clearly demonstrate the contribution of TLR stimulation to T-ALL progression in vivo.

Example 8

Figure 16C:
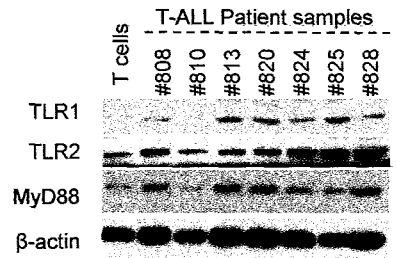

T-ALL Cells from Leukemia Patients Express TLR1 and TLR2 and Proliferate in Response to TLR1-TLR2 Agonist Because TLR1-TLR2 agonist administration augmented T-ALL expansion in vitro and in vivo, we examined TLR1 and TLR2 protein expression levels in cells from patients with T-ALL. Whereas TLR1 was variably expressed on 6 of 7 samples, TLR2 was highly expressed on all samples (FIG. 6A, FIG. 16C). As a control, the expression of TLR1 and TLR2 on primary T cells from healthy donors was examined. A representative western blot of 1 of 7 healthy donors tested is also shown in (FIG. 6A, FIG. 16C). In general, the expression of TLR1 on primary T cells from healthy donors was low to undetectable, whereas TLR2 was present, but generally at lower levels than those found in T-ALL samples.

The proliferative effects of TLR1-TLR2 agonists were examined in five T-ALL patient samples. Two of five samples exhibited increased proliferation in response to TLR1-TLR2 ligand (FIG. 6B; p<0.01; at concentrations above 1.25 µg/ml). Both TLR1 and TLR2 were detected in all five samples examined, but only 2 of 5 samples responded, indicating that TLR expression on T-ALL cells is not sufficient to induce proliferation. The three samples that did not respond to the TLR1-TLR2 agonist demonstrated a much higher basal proliferation as compared with those patient samples that responded to TLR1-2 ligand.

Example 9

T-ALL Cells from Leukemia Patients Express Phosphorylated IRAK-1,-4 and its Inhibition Reduces Proliferation The levels of total and phosphorylated IRAK-4 were examined in eight T-ALL samples. IRAK-4 was detected in healthy control primary T cells and in all T-ALL samples, albeit at variable levels (FIG. 6C; FIG. 11B). Multiple transcript variants encoding different IRAK-4 isoforms have been identified (Gene ID: 51135). At least three distinct IRAK-4 bands were detected in 5 T-ALL samples, whereas only two distinct bands were detected in healthy T cells (1 of 5 healthy donors is shown in the western blot). In addition, a smaller band was detected in T-ALL samples but not in primary T cells. Furthermore, five of eight patient samples expressed elevated levels of phosphorylated IRAK-4 in the absence of TLR agonist (FIG. 6C; FIG. 11B). In contrast, p-IRAK-4 was not detected in healthy T cells. The effects of IRAK-1,-4 inhibitors on T-ALL proliferation, specifically in samples with phosphorylated IRAK-1,-4, were examined. Every sample exhibited reduced proliferation in response to IRAK-1,-4 inhibitors, as compared to cells treated with an equal volume of vehicle DMSO (FIG. 6D). T-ALL samples expressing low levels of p-IRAK-4 showed high degree of sensitivity to DMSO alone whereas, those cells expressing low levels of p-IRAK-4 demonstrated resistance to DMSO Patient samples with higher p-IRAK-4 levels were more sensitive to IRAK-1,-4 inhibitors than those with lower p-IRAK-4 levels (FIG. 11C and FIG. 11D) suggesting that these cells had a greater dependence on IRAK signaling.

Example 10

Figure 12:
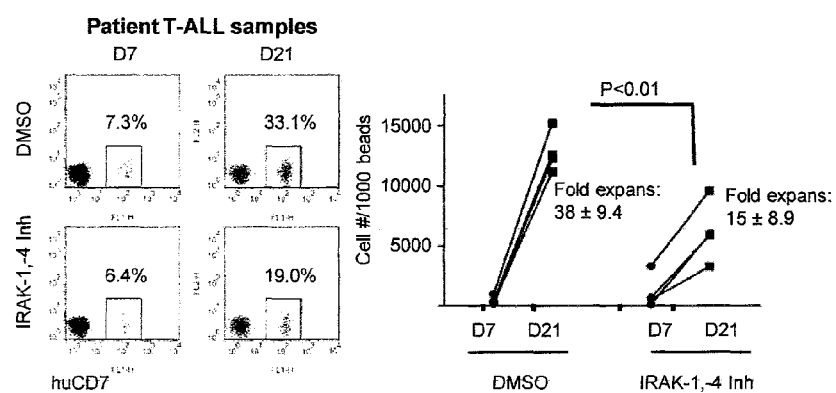
FIG. 12. Treatment with IRAK-1,-4 inhibitors reduces T-ALL numbers in vivo. NSG mice were irradiated (400 cGy) one day prior to intravenous injection of patient T-ALL cells (6×10$^6$ cells/mouse). Once 100 T-ALL cells/ul of blood were detected, mice were received one intraperitoneal injection with IRAK-1,-4 inhibitor (10 mg/Kg) or an equal volume of control vehicle (DMSO) on days 7, 10 and 13. Numbers of T-ALL cells (CD7$^+$) in peripheral blood were determined on day 27 and D21 by flow cytometry as described in FIG. 1. All the data shown are representative of two independent experiments (±SD) with three mice per group. Representative dot plots from bone marrow are shown in A (left panel). ANOVA; *P<0.05.

IRAK-1,-4 Inhibitor Reduces Cell Number by Mediating Cell Cycle Arrest, but not Apoptosis It was investigated whether the reduced proliferation that we observed with IRAK-1,-4 inhibitor (FIG. 11 and FIG. 12) was a result of cell cycle arrest or apoptosis. CCRF-CEM cells were treated with IRAK-1,-4 inhibitor for 24, 48, 72, and 96 hours. (FIG. 14.) IRAK-1,-4 inhibitor inhibited CCRF-CEM proliferation, but maintained a relatively constant number of viable cells throughout the time course examined (FIG. 14A and FIG. 14B). Analyses of cell cycle showed that the percentage of cells in G0/G1 phase increased from 25% to 43% within 24 hours of adding IRAK inhibitor and increased to 50% after 96 hours (FIG. 14C). The percentage of cells in S phase also decreased nearly 30% following IRAK inhibitor treatment (FIG. 14C). Analysis of the percentage of cells in sub-G1 phase and of cells labeling with Annexin V indicated that IRAK-1,-4 inhibitor did not induce apoptosis (FIG. 14D). These data show that reduction in T-ALL cell number in response to IRAK-1,-4 inhibition occurs through mechanisms that induce cell cycle arrest, but not apoptosis.

Example 11

IRAK-1,-4 Inhibition Induces a Cellular Senescence-Like Phenotype

Prolonged cell cycle arrest without apoptosis is reminiscent of cellular senescence. The expression of senescence-associated (SA)-β-gal in IRAK-1,-4 inhibitor-treated and DMSO-treated CCRF-CEM cells was measured. A nearly three-fold increase of SA-β-gal activity was detected within 48 hours of IRAK inhibitor treatment and maintained throughout the 96 hour time course evaluated (FIG. 15A). Twenty-six percent (±5%) of cells treated with the small molecule IRAK inhibitor were SA-β-gal positive as demonstrated by flow cytometry (FIG. 15B). Similarly, patient T-ALL samples collected from IRAK-1,-4 inhibitor-treated NSG mice also showed increased SA-β-gal activity (FIG. 15C; $p<0.05$). Although the changes in SA-β-gal in IRAK-1,-4 inhibitor patient samples were statistically different than control samples these differences were not as pronounced as in cell lines. This may be due to the fact that SA-β-gal activity in patient samples was conducted using protein samples that had been preserved at −80° C. for several weeks as compared with using fresh protein samples obtained from cell lines.

To further study the role of IRAK-1,-4 signaling in cellular senescence, we compared the expression of 84 key genes involved in the initiation and progression of senescence. The array results showed that six genes, CDKN1C, COL1A1, EGR1, ID1, PLAU and SERPINES, were significantly up- or down-regulated in IRAK-1,-4 inhibitor treated CCRF-CEM cells. All genes except COL1A1 were validated by RT-PCR and showed similar changes as to the array data; COL1A1 transcript levels however were similar between samples when examined by RT-PCR (FIG. 15D). Expression levels of CDKN1C, EGR1 and ID1 were also altered in all four T-ALL patient samples collected from IRAK-1,-4 inhibitor-treated NSG mice (FIG. 15E). Furthermore, two patient samples also demonstrated a down-regulation of PLAU and SERPINE1. None of patient samples showed changes in COL1A1 gene transcript levels.

Example 12

IRAK-1,-4 Inhibitor Works in Synergy with Other Chemotherapeutics

The T-ALL cell line CCRF-CEM was cultured in the presence of 0, 1.2, 5, 10, and 20 μM IRAK-1,-4 inhibitor. (FIG. 23). To each concentration of IRAK-1,-4 inhibitor titrating doses of ABT-737 (1000→15 nM) vincristine, VS (10→0.1 nM), and paclitaxol, PAC (100→1.5 nM). No synergist effect occurred between IRAK-1,-4 inhibitor and oligomicin, Oligo (20→0.3 μM). Apoptosis was measure 48 hours later by staining cells with 7AAD and analyzed by flow cytometry.

B. Melanoma Cell Lines

Example 13

Methods and Materials for Melanoma Cell Lines

Human melanoma cell lines were obtained from American Type Culture Collection. Melanoma cell lines were initially expanded and cryopreserved within one month of receipt. Cells were used for 6 months at which time a fresh vial of cryopreserved cells was used. Malme-3M cells were maintained in Iscove's Modified Dulbecco's Medium, SK-MEL-2, WM115, C32, and RPMI-7951 in Eagle's Minimum Essential Medium, A375 in Dulbecco's Modified Eagle's Medium, and G361 in McCoy's Sa Medium Modified. All media were purchased from Invitrogen Life Technologies (Grand Island, N.Y.) and supplemented with FBS, penicillin and streptomycin according to culture media recommended by ATCC.

Western Blot and Immunohistochemical Staining

Total cell extracts were prepared from melanoma cells. Proteins (20-30 µg/lane from cell lines) were resolved in Tris-glycine sodium dodecyl sulfate (SDS) gels and transferred to polyvinylidene difluoride membranes. The membrane was blocked for four hours with 5% milk in phosphate-buffered saline and 0.05% Tween-20, followed by incubation with antibodies against TLR1 (N-23), phosphorylated (p)-IRAK-1 (Ser 376), total IRAK-1 (H-273) (Santa Cruz Biotech, Santa Cruz, Calif., USA); TLR2, TLR4, TLR7, TLR9, TRIF, IRAK-M, IRAK-4, Tollip, GAPDH, (14C10) and -actin (Cell signaling, Danvers, Mass., USA); TLR3/CD283, TLR5 (IMGENEX, San Diego, Calif., USA); TLR6 (3D10H11), TLR8 (44C143), TLR10, MyD88 (Abcam, Cambridge, Mass., USA), Poly (ADP-ribose) polymerase (PARP), caspase-3 (Cell Signaling), overnight at 4° C. and, subsequently, incubated with horseradish peroxidase-conjugated secondary antibody, and detected using enhanced chemiluminescence (ECL Plus; Amersham Pharmacia Biotech). Melanoma tissue arrays were purchased from US Biomax, Inc (Rockville, Md.). For immunohistochemical staining samples were stained with mouse monoclonal anti-human phosphor-IRAK.-4 antibody (Abnova; dilution, 3.5 µg/ml) or normal mouse serum. Tissue histology sections (5-µm-thick) were deparaffinized, hydrated, heated in boiling 10 mmol/L sodium citrate (pH 6.0), for antigen retrieval, for 30 min and washed in Tris buffer. Peroxide blocking was done with 3% H102 in methanol at room temperature for 15 min, followed by 10% fetal bovine serum in TBS-t for 30 min at room temperature. Primary antibody incubation was done overnight at 4° C. Secondary antibody incubation with horse anti-mouse (1:200; Vector Laboratories, Burlingame, Calif.) was done for 1 hr, followed by application of diaminobenzidine chromogen for 5 min. The slides were then counterstained with hematoxylin and topped with a coverslip. IHC specimens were analyzed using "quick score" system in which the intensity of the immunohistochemical reaction was scored by multiplying the intensity 1 (weak), 2 (moderate), and 3 (strong) and the proportion of cells staining positively 0 (<10%), 1 (10-25%), 2 (26-50%), 3 (51-75%) or 4 (>75%).

A375 Melanoma Xenograft Model

NOD.Cg-Prkdc$^{scid}$ Il2rg$^{tmWJZ}$; SzJ IL2RG (NSG) mice (Jackson Laboratories, Bar Harbor, Me.) were subcutaneously (s.c.) injected with 2.5×10$^6$ A375 melanoma cells delivered in PBS. Use of mice was approved by the Institutional Animal Care and Use Committee. When tumors reached a size of approximately 50 mm$^2$ mice were injected intratumorally (i.t.) with 35 mg/kg of IRAK-1,-4 inhibitor or an equal volume of vehicle (DMSO). Mice were intraperitoneally (i.p.) injected with vinblastine (0.25 mg/kg) every 2 days for 5 days starting on the same day that mice received with IRAK-1,-4 inhibitor. Tumor sizes were analyzed using a mixed model approach for repeated measurements and mouse survival data were analyzed with the exact log-rank test.

TLR Agonists, IRAK Inhibitor, Chemotherapies and Flow Cytometry

The TLR1-TLR2 ligand tripalmitoyl-S-(bis(palmitoyloxy)propyl)-Cys-Ser-(Lys)3-Lys (Pam$_3$Cys) was purchased from Invivogen (San Diego, Calif., USA). In some experiments we used the IRAK.-1,-4 inhibitor (EMD Millipore, Darmstadt, Germany) which is a cell-permeable benzimidazole compound that selectively inhibits IRAK-1 and IRAK-4 and exhibits little activity against a panel of 27 other kinases. In some experiments cells were treated with the indicated concentrations of IRAK.-1,-4 inhibitor and vinblastine, cisplatin, and 5-fluorouracil (Sigma-Aldrich, St. Louis, Mo.), and apoptosis was quantitated by flow cytometry after staining cells with FITC-labeled annexin-V (BD Pharmingen, San Jose, Calif.) and propidium iodide (PI; Sigma-Aldrich).

Example 14

TLR Expression Profiles on Melanoma Cell Lines

Previous reports demonstrated the presence of TLR mRNA transcripts and a limited number of TLRs by flow cytometry on human melanomas (3,5). The expression profiles of TLR1-TLR 10 and several TLR-related signaling proteins were examined on various melanoma cell lines by Western blot. With the exception of C32 and Malme-3M cells, all melanoma cells expressed relatively high but variable levels of TLR1 (FIG. 7A). Appreciable levels of TLR2 and TLR3 were detected in SK-Mel-2 and A375 cells. TLR3 was also moderately expressed on RPMI-7951 and G361 cells. Most cell lines expressed detectable but variable levels of TLR4 and TLR7. TLR5 was strongly expressed on SK-Mel, WM1 15 and A375, moderately expressed on G361 and Malm-3M, but weakly detected on C32 and RPMI-7951. TLR8 levels were low on SK-Mel-2 and A375. TLR9 was strongly expressed on SK-Mel-2 and WM115 and moderately expressed on Malm-3M and G361. TLR10 expression was weak and variable on the different cell lines. All cell lines expressed the TLR adapter molecules MyD88 and TRIF.

Figure 22A:
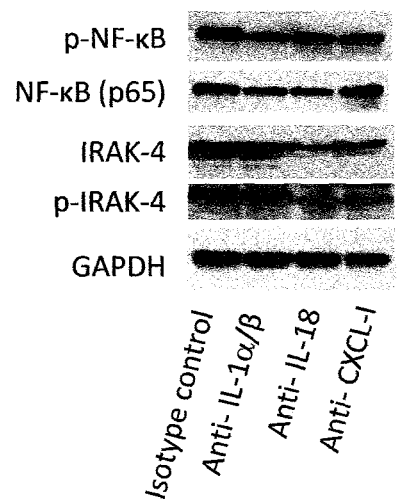
FIG. 22. Effects of TLR stimulation and cytokines on IRAK phosphorylation in melanoma cells. (A) A375 cells were cultured in the presence of anti-IL-18, anti-CXCL-1, (R&D Systems), anti-IL-1 (BioLegend), or mouse IgG (Sigma-Aldrich) all at 10 μg/ml. Forty-eight hours later the levels of the indicated proteins were determined by western blot. (B) A375 cells, which express p-IRAK-1 and p-IRAK-4, and G361 melanoma cells, which express very low levels of p-IRAK-1 (and express TLR5) were cultured in the presence of TLR1-TLR2 agonist (Pam$_3$CysK$_4$; 2.5 μg/ml) or TLR5 (flagellin; 100 ng/ml; InVivogen). Forty-eight hours later total protein was collected and the levels of the indicated proteins were examined by western blot.
Figure 22B:
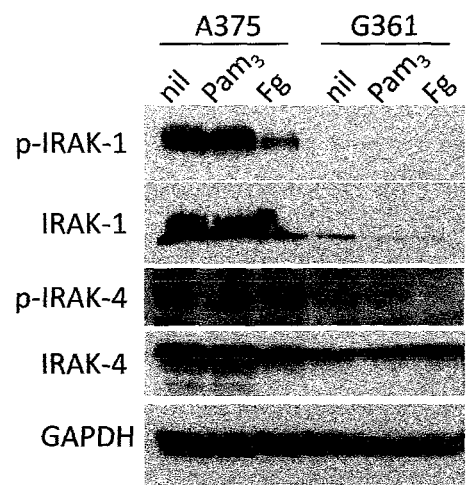

IRAK-1 and IRAK-4 play a central role in TLR-mediated signaling. All of the melanoma lines expressed high levels of IRAK-4 whereas variable levels of IRAK-1 were detected in all cell lines (FIG. 7A). The activated form of IRAK-1 (phosphorylated at serine 376; p-IRAK-1) was strongly expressed in Malme-3M, SK-MEL-2, and A375 specifically in the absence of exogenous TLR agonists. Similarly, variable levels of p-IRAK-4 (at threonine 345) were detected in melanoma cells (FIG. 7A). It was also examined whether TLR stimulation could augment p-IRAK levels in cells that expressed IRAK or induce p-IRAK in cells deficient in this protein. However, p-IRAK levels in A375 cells, which express relatively high p-IRAK-1 and p-IRAK-4, remained unchanged following TLR1-TLR2 stimulation suggesting that phosphorylated levels may already be at or near the maximum. A3375 cells were cultured in the presence of anti-IL-1, anti-CXCL-1, anti-IL_1, or mouse IgG all at 10 µg/ml. Forty-eight hours later the levels of the indicated proteins were determined by western blot. (FIG. 22A). In A375 cells, which express p-IRAK-1 and p-IRAK4, and G361 cells, which express low levels of p-IRAK-1 (and which express TLR5), neither TLR-1-TLR2 agonist (Pam$_3$CysK$_4$), nor TLR5 (Flagellin) stimulation increased or induced p-IRAK-1 or p-IRAK-4 expression levels. (FIG. 22B). The TLR5 agonist Flagellin reduced total and p-IRAK-4 levels in both cell lines.

The constitutive expression of phosphorylated IRAK-1 and IRAK-4 are demonstrated here on human cutaneous melanoma cells. These data also represent a comprehensive protein expression profile of TLRs and TLR-signaling proteins on melanoma cells and highlight the differences in the expression levels of these proteins in different melanoma lines.

Example 15

Cytokine/Chemokine Production by Melanoma Cells Following Activation or Inhibition of IRAK-1,-4

Figure 18A:
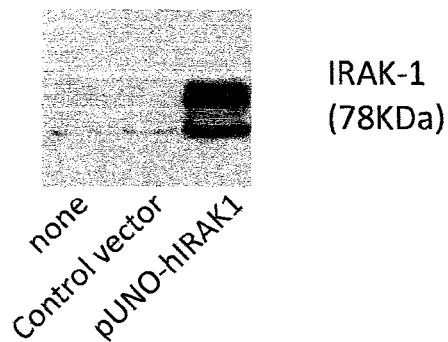
FIG. 18. Overexpressing IRAK-1 in melanoma cells augments the expression of various cytokines and chemokines. (A) G361 melanoma cells, which express very low to undetectable levels of IRAK-1, were transiently transfected via electroporation with pUNOHIRAK-1 (5 μg). (B) G361-pUNO-IRAK1 cells were cultured for 48 hours at which time supernatants were collected and cytokines/chemokines were analyzed using a Milliplex 42-array.
Figure 18B:
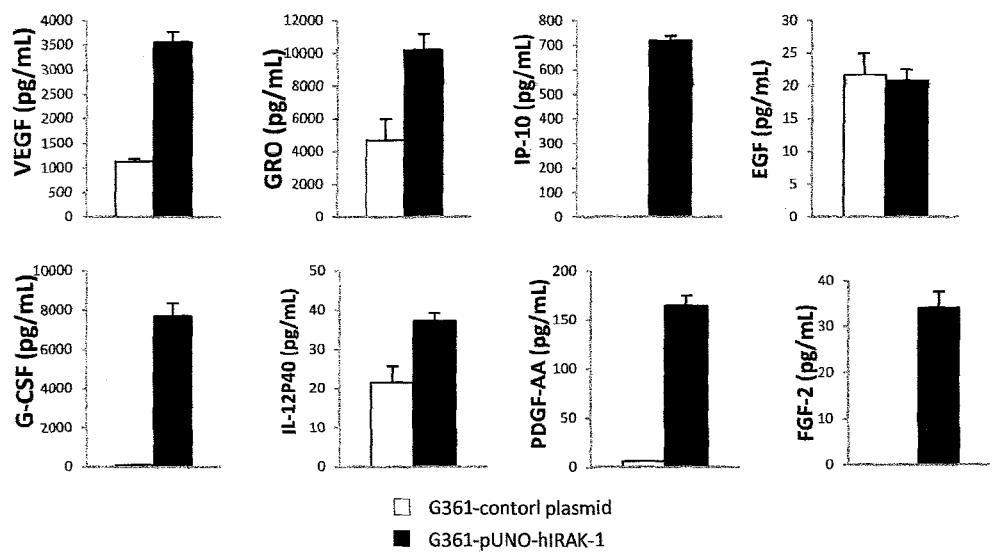

The stimulation of TLR-MyD88 or IL-I/18-MyD88 activates IRAK-1,-4 resulting in the transcription of various NF-KB-dependent genes, such as chemokines and cytokines as well as genes involved in cell survival. In A375 melanoma cells, the TLRI-TLR2 agonist $Pam_3CysK_4$ significantly augmented the levels of various cytokines and chemokines including those associated with angiogenesis such as vascular endothelial growth factor (VEGF) as well as the chemokine ligand-1 (CXCLI) and IL-8 which promote cell survival and proliferation (FIG. 7B; p<0.05; ANOVA) (12-14). The levels of granulocyte-macrophage colony stimulating factor (GM-CSF) and IP-10 were significantly increased following addition of the TLRI-TLR2 agonist (FIG. 7B; p<0.001; ANOVA). TLRI-TLR2 appeared to alter the levels of other MCP-I, IL-6 and fractalkine however these changes were not statistically significant. IRAK-1 was transiently overexpressed in G361 melanoma cells and changes in cytokine/chemokine levels were compared with control G361 cells. G361 melanoma cells, which express very low to undetectable levels of IRAK-1, were transiently transfected via electroporations with pUNO-hIRAK-1 (5 µg; Invovigen). (FIG. 18A). G361-pUNO-IRAK1 cells were cultured for 48 hours at which time supernatants were collected and cyttkines/chemokines were analyzed using a Milliplex 42-array. (FIG. 18B). Overexpressing IRAK-1 increased the levels of various cytokines/chemokines including VEGF, CXCL1, G-CSF, and IL-12p40. IRAK-1 expression also induced the expression of IP-10, GCSF, and PDGF-AA but had no effect on EGF production, as shown in FIG. 18. Collectively, these data indicate that melanoma cells express a functional TLR-IRAK signaling pathway and that the activation of this pathway might play a role in promoting cell survival or proliferation in part through the production and chemokines/cytokines.

Figure 19:
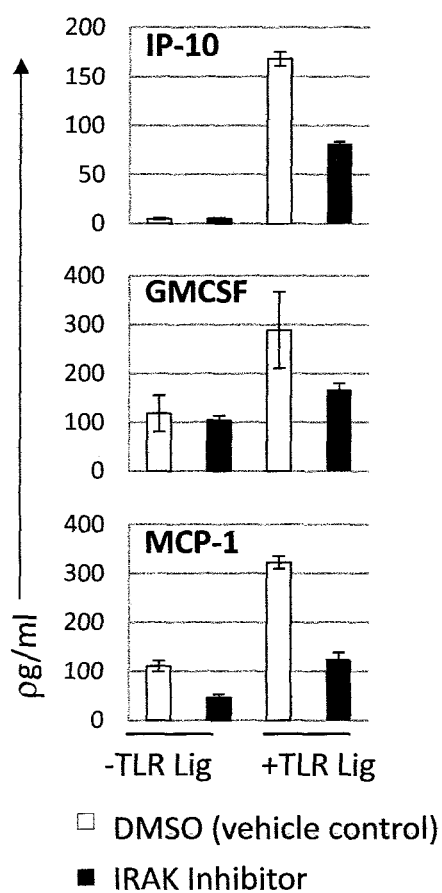
FIG. 19. Inhibiting IRAK-1/-4 abrogates the effects of TLR1-TLR2 agonist in melanoma cells. A375 cells were cultured in the presence or absence of TLR1-TLR2 ligand Pam$_3$CysK$_4$ (2.5 μg/ml) and in the presence of the IRAK-1/-4 inhibitor (10 μM) or vehicle control DMSO. Cytokine and chemokine production by was determined using a Milliplex cytokine/chemokine array 48 hrs. later.

On the basis that melanoma cells exhibited increased levels of phosphorylated IRAK-I and IRAK-4 and that the TLRI-TLR2 agonist increased the production of chemokines/cytokines the outcome of inhibiting IRAK signaling in melanoma cells was examined. Melanoma cells cultured in the presence of an IRAK-1,-4 inhibitor showed marked reduction of phosphorylated NF-KB (p-NF-KB) as compared with cells treated with vehicle alone (DMSO), (FIG. 7C). Furthermore, IRAK-1,-4 inhibition significantly reduced the production of VEGF, CXCLI, monocyte chemotactic protein-1 (MCP 1), platelet-derived growth factor alpha (PDGF-A) and fibroblast growth factor (FGF-2) in A375 cells (FIG. 7D, p<0.05). IRAK-1,-4 inhibition reduced the levels of these molecules in the absence of TLR agonists suggesting that in addition to playing a critical role in TLR signaling, IRAK-1,-4 contributes to cell survival and/or expansion in a TLR-independent fashion. Notably, the addition of IRAK-1,-4 inhibitors also decreased the effects of TLR1-TLR2 agonist (FIG. 19) further confirming that changes in chemokines/cytokines occurred in a TLR-MyD88-IRAK fashion. A375 cells were cultured in the presence or absence of TLR1-TLR2 ligand $Pam_3CysK_4$ (2.5 µg/ml) and in the presence of the IRAK-1,-4 inhibitor (10 µM) or vehicle control DMSO. (FIG. 19). Therefore, activation of IRAK-1,-4 signaling on melanoma cells in vivo might contribute to cancer progression by inducing the expression of various chemokines and cytokines beneficial to cancer cell survival, division, and/or angiogenesis. Furthermore, the inhibition of IRAK-1,-4 drastically reduced NF-KB activation and the production of several cytokines/chemokines, indicating that IRAK-1,-4 signaling plays a central role in cytokine/chemokine production even in absence of exogenous TLR agonists.

Example 16

IRAK Inhibition Sensitizes Melanoma Cells to Certain Chemotherapies In Vitro and In Vivo Melanoma cells become resistant against a variety of chemotherapies by altering their cell division and survival signaling pathways during cancer progression (15). Various studies have documented the pro survival and proliferative effects that TLR signaling has on different cell types (11). Considering the impact that inhibiting IRAK-1,-4 had on NF-KB activation and chemokine/cytokine production, it was explored whether treatment of melanoma cells with IRAK-1,-4 inhibitor sensitized them to the toxic effects of vinblastine. Apoptosis was examined by flow cytometry. Melanoma cell lines A375 and Malme-3M cultured in the presence of 2.5 µmol/L of IRAK-1,-4 inhibitor and various 0-200 nmol/L concentrations of vinblastine demonstrate increased sensitivity to this chemotherapeutic drug (FIG. 8A, left panels). The addition of 0-100 nmol/L 5'-fluorouracil and IRAK-1,-4 inhibitor also appeared to enhance apoptosis of Malme3M cells but not A375 cells (FIG. 8A, middle panels). IRAK-1,-4 inhibitor did not increase 0-50 nmol/L cisplatin's cytotoxicity in either cell line (FIG. 8A, right panels).

A375 cells were transfected via electroporation with siRNA-IRAK-1,-4. IRAK-1 protein levels were examined by Western blotting. FIG. 8B. A375-control, A375-psiRNA-hiRAK-1, A375 psiRNA-hiRAK-4, or cells expressing both psiRNA-hiRAK-1 and -4 were cultured in the presence of 100 nmol/L vinblastine for 48 hours and apoptosis was examined by flow cytometry. IRAK inhibitor alone or cells expressing psiRNA-IRAK moderately increased melanoma apoptosis (in the absence of vinblastine), suggesting that IRAK signaling plays an important role in cell survival.

Figure 20A:
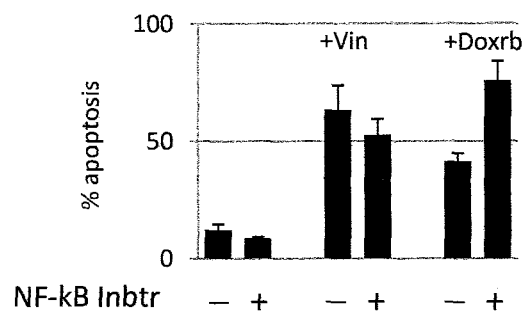
FIG. 20. Role of TLR-induced cytokines and NF-kB on cell survival. (A) A375 melanoma cells were cultured in a 48-well plates in the presence or absence of NF-kB inhibitor NF-kB inhibitor SN50 (100 nM; Anaspec) with or without vinblastine (100 nM) or Doxorubicin (0.25 μg/ml). The percentage of apoptotic cells was measured by staining cells with Annexin and PI 48 hours later and analyzed by flow cytometry. (B) C32 melanoma cells were cultured in the presence of vinblastine (100 nM) and in the absence or absence of TLR1-TLR2 ligand (2.5 μg/ml) or the presence of supernatant from TLR1-TLR2-stimulated A375 cells. After 48 hours, apoptosis was measured by flow cytometry. (C) A375 melanoma cells were cultured in the presence or absence of vinblastine (100 nM) and IL-1 (50 ng/ml; BioLegend), IL-18 (100 ng/ml; Medical and Biological Lab) or CXCL1 (50 ng/ml; R&D Systems). Apoptosis was measured 48 hours later by flow cytometry.

IRAK-1,-4 inhibition resulted in reduced levels of activated NF-Kβ (FIG. 7C). Therefore, it was explored whether IRAK-NF-Kβ signaling is linked to chemoresistance by treating A375 melanoma cells with and without NF-Kβ inhibitor and in the absence and presence of vinblastine. NF-Kβ inhibition did not alter A375's sensitivity to vinblastine (FIG. 20A). The effects of inhibiting NF-Kβ in A375 melanoma cells were also examined. In sharp contrast to the combinatorial effects of NF-Kβ inhibition plus vinblastine, NF-Kβ inhibition increased the toxic effects of doxorubicin on A375. (FIG. 20A).

Figure 20B:
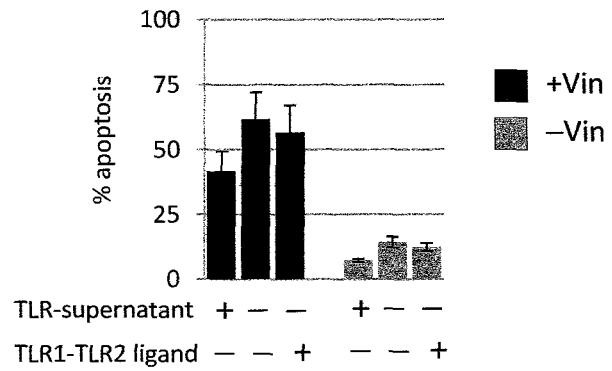

Alternatively, cytokines/chemokines produced in response to TLR-IRAK signaling might also contribute to the chemoprotective effects. Supernatant from TLR-1-TLR-2 stimulated or unstimulated A375 melanoma cells was added to the C32 melanoma cells in the presence or absence of vinblastine. Another group of cells were treated with TLR1-TLR2 ligand and apoptosis was examined by flow cytometry. FIG. 20B shows that supernatant from TLR-stimulated A375 cells moderately reduced vinblastine-induced apoptosis as compared with untreated cells (P<0.05; ANOVA), whereas TLR1-TLR2 ligand had little effect.

Figure 20C:
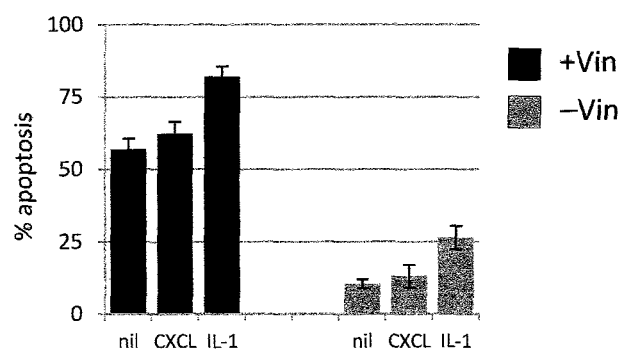

Neither IL-1 nor CXCL1 appeared to be the cytokines responsible for the observed chemoprotective effects. (FIG. 20C).

Western blot analysis was conducted using antibodies specific for caspase-3 and PARP as an independent biochemical assay to confirm that A375 melanoma cells triggered apoptosis. Active caspase-3, which is cleaved to yield catalytically active subunits, was detected following the addition of 10 µM IRAK-1,-4 inhibitor (FIG. 8C). Enhanced accumulation of cleaved PARP, which is targeted for caspase-dependent proteolysis, was also observed in IRAK-1,-4 inhibitor-treated cells. Increased levels of cleaved PARP and caspase-3 occurred in a concentration-dependent manner (FIG. 8C). As shown in FIG. 8D, the combination of vinblastine and 2.5 µmol/L of IRAK-1,-4 inhibitor also increased the levels of cleaved PARP and caspase-3. In contrast, treatment with vinblastine or IRAK-1,-4 inhibitor alone had little effect on the levels of these molecules. The expression of various apoptosis-related genes in A375 melanoma cell line treated with DMSO vehicle (control), IRAK inhibitor, and vinblastine, was compared and a gene profile was observed that favored apoptosis in the presence of inhibitor alone or vinblastine. (FIG. 21).

The anti-tumor effects of combinatorial therapy using vinblastine and IRAK-1,-4 inhibitor were tested in vivo. A375 cells were subcutaneously (s.c.) injected into NSG mice and grown to 30-50 mm². Mice were injected intraperitoneally with vinblastine or intratumorally with IRAK-1,-4 inhibitor (35 mg/kg) or with vinblastine or IRAK-1,-4 inhibitor alone. Mice receiving IRAK-1,-4 inhibitors plus vinblastine showed a marked reduction in tumor growth and improved mouse survival (median survival: 38 days) as compared with mice receiving vehicle (DMSO) plus vinblastine (median survival: 22 days) or mice receiving IRAK-1,-4 inhibitor (median survival: 19 days), (FIGS. 9A-9B). Mice receiving single therapy of IRAK-1,-4 inhibitor or vinblastine showed modest tumor growth delay but similar survival as compared with control mice (median survival: 17 days). Despite their tumor growth delay, mice receiving IRAK-1,-4 inhibitors plus vinblastine succumbed to tumor challenge by 40 days after initiation of treatment. These results emphasize the anti-tumor effects of combinatorial therapy and highlight the need for further optimization.

Example 17

Phosphorylated IRAK-4 in Melanoma Biopsies

Phosphorylated IRAK-4 expression was analyzed by immunohistochemistry in normal skin and in melanoma tissue derived from patients at various clinical stages. While little staining was observed in normal skin, p-IRAK-4 was highly expressed in melanoma samples (representative staining are shown in FIG. 10A). We sought to determine the association between p-IRAK-4 expression and the clinical stage. As shown in FIG. 10B, p-IRAK-4 levels were not linked to melanoma stage nor was there a correlation between p-IRAK-4 levels and metastasis. Quantification of the staining, however, revealed two distinct groups in melanoma samples in all clinical stages; one group of melanoma samples expressed p-IRAK-4 levels similar to those on normal skin and another group expressed significantly higher p-IRAK-4 levels (FIG. 10B; p<0.005; ANOVA). Samples from stage I and IV melanoma also showed a distinct division between high and low/no expression of phosphorylated IRAK-4 despite the limited number of samples (FIG. 10B; p<0.05; ANOVA). Of the 242 melanoma samples analyzed nearly half expressed elevated levels of p-IRAK-4. The elevated levels of p-IRAK-4 in melanoma patients did not correlate with patient age or gender (FIG. 10C).

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application (including the reference lists) are hereby expressly incorporated by reference as if set forth herein in their entirety, except where terminology is not consistent with the definitions herein. Although specific terms are employed, they are used as in the art unless otherwise indicated.

REFERENCES

1. Dores G M, Devesa S S, Curtis R E, Linet M S, Morton L M. Acute leukemia incidence and patient survival among children and adults in the United States, 2001-2007. Blood 2012 Jan. 5; 119(1):34-43.
2. Faderi S, O'Brien S, Pui C H, Stock W, Wetzler M, Hoelzer D, et al. Adult acute lymphoblastic leukemia: concepts and strategies. Cancer 2010 Mar. 1; 116(5): 1165-76.
3. Pui C H, Evans W E. Acute lymphoblastic leukemia. N Engl J Med 1998 Aug. 27; 339(9):605-15.
4. Goto Y, Arigami T, Kitago M, Nguyen S L, Narita N, Ferrone S, et al. Activation of Toll-like receptors 2, 3, and 5 on human melanoma cells induces inflammatory factors. Mol Cancer Ther 2008; 7; 36 42-53.
5. Molteni M, Marabella D, Orlandi C, Rossetti C. Melanoma cell lines are responsive in vitro to lipopolysaccharide and express TLR-4. Cancer Lett 2005; 235: 75-83.
6. Saint-Jean M, Knol A C, Nguyen J M, Khammari A, Dreno B. TLR expression in human melanoma cells. Eur J Dermatol 2011; 21: 899-905.
7. Salaun B, Lebecque S, Matikainen S, Rimoldi D, Romero P. Toll-like receptor 3 expressed by melanoma cells as a target for therapy? Clin Cancer Res 2007; 13; 4565-74.
8. Cao Z, Henzel W J, Gao X. IRAK: a kinase associated with the interleukin-1 receptor. Science 1996; 271:1128-31.
9. Li S, Strelow A, Fontana E K, Wesche H. IRAK-4: a novel member of the IRAK family with the properties of an IRAK-kinase. Proc Natl Acad Sci USA 2002; 99: 5567-72.
10. Wang Z, Wesche H, Stevens T, Walker N, Yeh W C. IRAK-4 inhibitors for inflammation. Curr Top Med Chem 2009; 9: 724-37.
11. Cheng H, Addona T, Keshishian H, Dahistrand E, Lu C, Dorsch M, et al. Regulation of IRAK-4 kinase activity via autophorsrylation within its activation loop. Biochem Biophys Res Commun 2007; 352: 609-16.
12. Akira S, Takeda K. Toll-like receptor signaling. Nat Rev Immunol 2004; 4: 499-511.
13. Li X, Jiang S, Tapping R I. Toll-like receptor signaling in cell proliferation and survival. Cytokine 2010; 49: 1-9.
14. Mizobe T, Tsukada J, Higashi T, Mouri F, Matsuura A, Tanikawa R, et al. Constitutive association of MyD88 to IRAK in HTLV-I-transformed T cells. Exp Hematol 2007 December; 35(12):1812-22

15. Weng A P, Ferrando A A, Lee W, Morris J P, Silverman L B, Sanchez-Irizarry C, et al. Activating mutations of NOTCH I in human T cell acute lymphoblastic leukemia. Science 2004 Oct. 8; 306(5694):269-71.
16. Palaga T, Buranaruk C, Rengpipat S, Fauq A H, Golde T E, Kaufmann S H, et al. Notch signaling is activated by TLR stimulation and regulates macrophage functions. Eur J Immunol 2008 January; 38(1):174-83.
17. DeAngelo D J, Stone R M, Heaney M L, Nimer S D, Paquette R L, Klisovic R B, et al. Phase 1 clinical results with tandutinib (MLN518), a novel FLT3 antagonist, inpatients with acute myelogenous leukemia or high-risk myelodysplastic syndrome: safety, pharmacokinetics, and pharmacodynamics. Blood 2006 Dec. 1; 108(12):3674-81.
18. Real P J, Tosello V, Palomero T, Castillo M, Hernando E, de S E, et al. Gamma-secretase inhibitors reverse glucocorticoid resistance in T cell acute lymphoblastic leukemia. Nat Med 2009 January; 15(1):50-8.
19. Roy M, Pear W S, Aster J C. The multifaceted role of Notch in cancer. Curr Opin Genet Dev February; 17(1): 52-9.
20. Elzinga B M, Twomey C, Powell J C, Harte F, McCarthy J V. Interleukin-I receptor type 1 is a substrate for gamma-secretase-dependent regulated intramembrane proteolysis. J Biol Chem 2009 Jan. 16; 284(3):1394-409.
21. Smith T J, Yamamoto K, Kurata M, Yukimori A, Suzuki S, Umeda S, et al. Differential expression of Toll-like receptors in follicular lymphoma, diffuse large B-cell lymphoma and peripheral T-cell lymphoma. Exp Mol Pathol 2010 Aug. 25.
22. Jarrousse V, Quereux G, Marques-Briand S, Knol A C, Khammari A, Dreno B. Toll-like receptors 2, 4 and 9 expression in cutaneous T-cell lymphoma (mycosis fungoides and Sezary syndrome). Eur J Dermatol 2006 November; 16(6):636-41.
23. Suchin K R, Junkins-Hopkins J M, Rook A H. Treatment of stage IA cutaneous T-Cell lymphoma with topical application of the immune response modifier imiquimod. Arch Dermatol 2002 September; 138(9):1137-9.
24. Mollaki V, Georgiadis T, Tassidou A, Ioannou M, Daniil Z, Koutsokera A, et al. Polymorphisms and haplotypes in TLR9 and MYD88 are associated with the development of Hodgkin's lymphoma: a candidate-gene association study. J Hum Genet 2009 November; 54(11):655-9.
25. Purdue M P, Lan Q, Wang S S, Kricker A, Menashe I, Zheng T Z, et al. A pooled investigation of Toll-like receptor gene variants and risk of non-Hodgkin lymphoma. Carcinogenesis 2009 February; 30(2):275-81.
26. Nieters A, Beckmann L, Deeg E, Becker N. Gene polymorphisms in Toll-like receptors, interleukin-10, and interleukin-10 receptor alpha and lymphoma risk. Genes Immun 2006 December; 7(8):61 5-24.
27. Bohnhorst J, Rasmussen T, Moen S H, Flottum M, Knudsen L, Borset M, et al. Toll-like receptors mediate proliferation and survival of multiple myeloma cells. Leukemia 2006 June; 20(6): 1138-44.
28. Matzinger P. Tolerance, danger, and the extended family. Annu Rev Immunol 1994; 12:991-1045.
29. Chen W, Syldath U, Bellmann K, Burkart V, Kolb H. Human 60-kDa heat-shock protein: a danger signal to the innate immune system. J Immunol 1999 Mar. I5; I62(6): 3212-8.
30. Wallin R P, Lundqvist A, More S H, von B A, Kiessling R, Ljunggren H G. Heat-shock proteins as activators of the innate immune system. Trends Immunol 2002 March; 23(3):130-5.
31. Vabulas R M, hmad-Nejad P, da C C, Miethke T, Kirschning C J, Hacker H, et al. Endocytosed HSP60s use toll-like receptor 2 (TLR2) and TLR4 to activate the toll/interleukin-1 receptor signaling pathway in innate immune cells. J Biol Chem 2001 Aug. 17; 276(33):31332-9.
32. Wheeler A, Archbold S M, Hardie T, Watson L M. Children with cochlear implants: the communication journey. Cochlear Implants Int 2009 March; 10(1):41-62.
33. vand H, I, Wilbrink B, Tchetverikov I, Schrijver I A, Schouls L M, Hazenberg M P, et al. Presence of bacterial DNA and bacterial peptidoglycans in joints of patients with rheumatoid arthritis and other arthritides. Arthritis Rheum 2000 March; 43(3):593-8.
34. Sobek V, Birkner N, Falk I, Wurch A, Kirschning C J, Wagner H, et al. Direct Toll-like receptor 2 mediated co-stimulation of T cells in the mouse system as a basis for chronic inflammatory joint disease. Arthritis Res Tuer 2004; 6(5):R433-R446.
35. Termeer C, Benedix F, Sleeman J, Fieber C, Voith U, Ahrens T, et al. Oligosaccharides of Hyaluronan activate dendritic cells via toll-like receptor 4. J Exp Med 2002 Jan. 7; 195(1):99-111.
36. Johnson G B, Brunn G J, Kodaira Y, Platt J L. Receptor-mediated monitoring of tissue well-being via detection of soluble heparan sulfate by Toll-like receptor 4. J Immunol 2002 May 15; 168(10):5233-9.
37. Cheng N, He R, Tian J, Ye P P, Ye R D. Cutting edge: TLR2 is a functional receptor for acute-phase serum amyloid A. J Immunol 2008 Jul. 1; 181(1):22-6.
38. Erridge C. Endogenous ligands of TLR2 and TLR4: agonists or assistants? J Leukoc Biol 2010 June; 87(6): 989-99.
39. Barth A, Wanek L A, Morton D L. Prognostic factors in 1,521 melanoma patients with distant metastases. J Am Coll Surg 1995 September; 181(3):193-201.
40. Tawbi H A, Buch S C. Chemotherapy resistance abrogation in metastatic melanoma. Clin Adv Hematol Oncol 2010 April; 8(4):259-66.
41. Goto Y, Arigami T, Kitago M, Nguyen S L, Narita N, Ferrone S, et al. Activation of Toll-like receptors 2, 3, and 4 on human melanoma cells induces inflammatory factors. Mol Cancer Tuer 2008 November; 7(11):3642-53.
42. Smith T J, Yamamoto K, Kurata M, Yukimori A, Suzuki S, Umeda S, Sugawara E, Kojima Y, Sawabe M, Nakagawa Y, Suzuki K, Crawley J T, et al. Differential expression of Toll-like receptors in follicular lymphoma, diffuse large B-cell lymphoma and peripheral T-cell lymphoma. Exp. Mol. Pathol. 2010.
43. Jarrousse V, Quereux G, Marques-Briand S, Knol A C, Khammari A, Dreno B. Toll-like receptors 2, 4 and 9 expression in cutaneous T-cell lymphoma (mycosis fungoides and Sezary syndrome). Eur. J. Dermatol. 2006; 16:636-41.
44. Suchin K R, Junkins-Hopkins J M, Rook A H. Treatment of stage IA cutaneous T-Cell lymphoma with topical application of the immune response modifier imiquimod. Arch. Dermatol. 2002; 138:1137-9.
45. Esplin B L, Shimazu T, Welner R S, Garrett K P, Nie L, Zhang Q, Humphrey M B, Yang Q, Borghesi L A, Kincade P W. Chronic exposure to a TLR ligand injures hematopoietic stem cells. J. Immunol. 2011; 186:5367-75.
46. Diego V P, Curran J E, Charlesworth J, Peralta J M, Voruganti V S, Cole S A, Dyer T D, Johnson M P, Moses E K, Goring H H, Williams J T, Comuzzie A G, et al. Systems genetics of the nuclear factor-kappaB signal transduction network. I. Detection of several quantitative trait loci potentially relevant to aging. Mech. Ageing Dev. 2012; 133:11-9.
47. Lin H, Yan J, Wang Z, Hua F, Yu J, Sun W, Li K, Liu H, Yang H, Lv Q, Xue J, Hu Z W. Loss of Immunity-supported senescence enhances susceptibility to hepatocellular carcinogenesis and progression in TLR2-deficient mouse. Hepatology 2012.
48. Astle M V, Hannan K M, Ng P Y, Lee R S, George A J, Hsu A K, Haupt Y, Hannan R D, Pearson R B. AKT induces senescence in human cells via mTORC1 and p53 in the absence of DNA damage: implications for targeting mTOR during malignancy. Oncogene 2012; 31:1949-62.
49. Guo X, Yu M, Kang X, Yin H. mTOR complex 2 activation by reconstituted high-density lipoprotein prevents senescence in circulating angiogenic cells. Arterioscler. Thromb. Vasc. Biol. 2011; 31:1421-9.
50. Kolesnichenko M, Hong L, Liao R, Vogt P K, Sun P. Attenuation of TORC1 signaling delays replicative and oncogenic RAS-induced senescence. Cell Cycle 2012; 11:2391-401.
51. Burgess D J. Senescence. NF-kappaB shows its beneficial side. Nat. Rev. Cancer 2011; 11:832-3.
52. Chien Y, Scuoppo C, Wang X, Fang X, Balgley B, Bolden J E, Premsrirut P, Luo W, Chicas A, Lee C S, Kogan S C, Lowe S W. Control of the senescence-associated secretory phenotype by NF-kappaB promotes senescence and enhances chemosensitivity. Genes Dev. 2011; 25:2125-36.
53. Salminen A, Kauppinen A, Kaarniranta K. Emerging role of NF-kappaB signaling in the induction of senescence-associated secretory phenotype (SASP). Cell Signal. 2012; 24:835-45.
54. Krones-Herzig A, Mittal S, Yule K, Liang H, English C, Urcis R, Soni T, Adamson E D, Mercola D. Early growth response 1 acts as a tumor suppressor in vivo and in vitro via regulation of p53. Cancer Res. 2005; 65:5133-43.
55. Redmond K L, Crawford N T, Farmer H, D'Costa Z C, O'Brien G J, Buckley N E, Kennedy R D, Johnston P G, Harkin D P, Mullan P B. T-box 2 represses NDRG1 through an EGR1-dependent mechanism to drive the proliferation of breast cancer cells. Oncogene 2010; 29:3252-62.
56. Besancenot R, Chaligne R, Tonetti C, Pasquier F, Marty C, Lecluse Y, Vainchenker W, Constantinescu S N, Giraudier S. A senescence-like cell-cycle arrest occurs during megakaryocytic maturation: implications for physiological and pathological megakaryocytic proliferation. PLoS. Biol. 2010; 8.
57. Krones-Herzig A, Adamson E, Mercola D. Early growth response 1 protein, an upstream gatekeeper of the p53 tumor suppressor, controls replicative senescence. Proceedings of the National Academy of Sciences of the United States of America 2003; 100:3233-8.
58. Giovannini C, Gramantieri L, Minguzzi M, Formari F, Chieco P, Grazi G L, Bolondi L. CDKN1C/P57 Is Regulated by the Notch Target Gene Hes1 and Induces Senescence in Human Hepatocellular Carcinoma. Am. J. Pathol. 2012; 181:413-22.
59. Hoffmann M J, Florl A R, Seifert H H, Schulz W A. Multiple mechanisms down-regulate CDKN1C in human bladder cancer. Int. J. Cancer 2005; 114:406-13.
60. Dabrowska M, Skoneczny M, Rode W. Functional gene expression profile underlying methotrexate-induced senescence in human colon cancer cells. Tumour. Biol. 2011; 32:965-76.
61. Huang B, Deo D, Xia M, Vassilev L T. Pharmacologic p53 activation blocks cell cycle progression but fails to induce senescence in epithelial cancer cells. Mol. Cancer Res. 2009; 7:1497-509.
62. Ling Y X, Tao J, Fang S F, Hui Z, Fang Q R. Down-regulation of Id1 by small interfering RNA in prostate cancer PC3 cells in vivo and in vitro. Eur. J. Cancer Prev. 2011; 20:9-17.
63. Schwarze S R, Fu V X, Desotelle J A, Kenowski M L, Jarrard D F. The identification of senescence-specific genes during the induction of senescence in prostate cancer cells. Neoplasia. 2005; 7:816-23.
64. Swarbrick A, Roy E, Allen T, Bishop J M. Id1 cooperates with oncogenic Ras to induce metastatic mammary carcinoma by subversion of the cellular senescence response. Proc. Natl. Acad. Sci. U.S.A 2008; 105:5402-7.

TABLE 1

Proliferative effects of TLR agonists on T-cell neoplasms.
Proliferative effects of TLR ligands on T-cell subsets

| | Acute Lymphoblastic Leukemia | | | | | | | | |
|---|---|---|---|---|---|---|---|---|---|
| | CCRF-CEM | CEM-C1 | CEM-C2 | CEM-C7 | Jurkat | Loucy | Molt-4 | HSB-2 | SupT1 |
| TLR1/2 (Pam3Cysk4) | + (1.2) | + (2.5) | + (2.5) | + (2.5) | o | + (2.5) | o | − (5) | o |
| TLR3 (pI:C) | o | o | o | − (10) | o | o | o | − (0.6) | − (2.5) |
| TLR4 (LPS) | o | o | − (5.0) | | o | o | o | − (0.3) | o |
| TLR5 (Flagellin) | o | o | o | − (2.5) | o | o | o | − (10) | o |
| TLR2/6 (HKML) | o | o | o | o | o | o | − (5.0) | − (5) | − (10) |
| TLR7 (Imiquimod) | o | o | o | o | − (10) | o | o | − (1.2) | − (0.6) |
| TLR8 (ssRNA) | o | o | o | o | o | + (5) | o | − (0.1) | − (5) |

TABLE 1-continued

Proliferative effects of TLR agonists on T-cell neoplasms.
Proliferative effects of TLR ligands on T-cell subsets

| | | | | | | | | | |
|---|---|---|---|---|---|---|---|---|---|
| TLR9 (CpG-ODN) | ○ | ○ | ○ | ○ | ○ | ○ | ○ | − (0.6) | − (1.2) |

| | Cutaneous T-cell Lymphoma/ T-cell Leukemia | | | | | Primary T-cells | |
|---|---|---|---|---|---|---|---|
| | Hut-78 | HH | Hut 102 | MO | H9 | Non-Act | Activated |
| TLR1/2 (Pam3Cysk4) | ○ | ○ | ○ | ○ | ○ | ○ | + (10) |
| TLR3 (pI:C) | ○ | ○ | − (10) | ○ | − (1.2) | ○ | ○ |
| TLR4 (LPS) | ○ | ○ | − (10) | − (5) | − (5) | ○ | ○ |
| TLR5 (Flagellin) | ○ | ○ | ○ | ○ | − (10) | ○ | + (10) |
| TLR2/6 (HKML) | ○ | ○ | ○ | ○ | − (2.5) | ○ | ○ |
| TLR7 (Imiquimod) | ○ | ○ | ○ | ○ | ○ | ○ | − (5) |
| TLR8 (ssRNA) | ○ | ○ | − (5) | − (10) | − (1.2) | ○ | − (5) |
| TLR9 (CpG-ODN) | ○ | ○ | − (5) | − (10) | − (0.6) | ○ | ○ |

TABLE 2

Primers for RT-PCR

| SEQ ID NO | Gene Name | Sequences | |
|---|---|---|---|
| 1 | CDKN1C | Forward | AGATCAGCGCCTGAGAAGTCGT |
| 2 | | Reverse | TCGGGGCTCTTTGGGCTCTAAA |
| 3 | COL1A1 | Forward | GATTCCCTGGACCTAAAGGTGC |
| 4 | | Reverse | AGCCTCTCCATCTTTGCCAGCA |
| 5 | EGR1 | Forward | AGCAGCACCTTCAACCCTCAGG |
| 6 | | Reverse | GAGTGGTTTGGCTGGGGTAACT |
| 7 | ID1 | Forward | GTTGGAGCTGAACTCGGAATCC |
| 8 | | Reverse | ACACAAGATGCGATCGTCCGCA |
| 9 | PLAU1 | Forward | GGCTTAACTCCAACACGCAAGG |
| 10 | | Reverse | CCTCCTTGGAACGGATCTTCAG |
| 11 | SERPINE1 | Forward | CTCATCAGCCACTGGAAAGGCA |
| 12 | | Reverse | GACTCGTGAAGTCAGCCTGAAAC |
| 13 | GAPDH | Forward | GTCTCCTCTGACTTCAACAGCG |
| 14 | | Reverse | ACCACCCTGTTGCTGTAGCCAA |
| 15 | B-ACTIN | Forward | AACTCCTGCTGGACAGACGATG |
| 16 | | Reverse | GATCAGTGCCATGTTCCAGCAAC |

TABLE 3

Changes in protein expression following IRAK-1,-4 inhibition in CCRF-CEM T-ALL cells.

| Protein Name | Fold Change |
|---|---|
| AFX(Ab-197) | −2.62 |
| AFX(Phospho-Ser 97) | −2.03 |
| BAD(Ab-112) | −1.76 |
| BAD(Phospho-Ser112) | −2.44 |
| BCL-XL(Phospho-Ser62) | −2.42 |
| CDC2(Phospho-Tyr15) | −2.33 |
| FKHR(Ab-319) | −2.54 |
| FKHRL1(Ab-253) | −2.36 |
| FKHRL1(Phospho-Ser253) | −2.53 |
| GSK3 alpha(Phospho-Ser21) | −2.13 |
| HSP27(Phospho-Ser15) | −2.20 |
| IKB-alpha(Ab-32/36) | −1.96 |
| IKB-alpha(Phospho-Ser32/Phospho-Ser36) | −2.95 |
| IRS-1(Phospho-Ser639) | −2.37 |
| JAK2(Phospho-Tyr221) | −2.05 |
| NFKB-p100/p52(Phospho-Ser869) | −2.50 |
| NFKB-p105/p50(Phospho-Ser337) | −4.06 |
| NFKB-p65(Ab-435) | −1.39 |
| NFKB-p65(Phospho-Thr435) | −2.39 |
| p44/42 MAP Kinase(Phospho-Tyr204) | −2.24 |
| p53(Ab-46) | −1.39 |
| p53(Phospho-Ser46) | −2.27 |
| PTEN(Phospho-Ser380) | 1.35 |
| Raf1(Phospho-Ser338) | −2.46 |
| STAT1(Phospho-Ser727) | −2.17 |
| STAT3(Phospho-Ser727) | −2.11 |

Total protein was collected from T-ALL cells after being cultured in the presence of IRAK-1,-4 inhibitor or DMSO for 72 hours. An antibody array was used to investigate the involvement of various apoptosis-related signaling molecules following addition of IRAK inhibitor. The fold changes in total or phosphorylated proteins were determined after normalization of protein levels to the housekeeping protein GAPDH. Only those proteins which demonstrated at least a three-fold increase above background levels were considered for analyses. A 1.8-fold-change was set as a cutoff value.

What is claimed is:

1. A method comprising administering an Interleukin-1 Receptor-Associated Kinase-1,-4 (IRAK-1,-4) inhibitor to a subject having a melanoma or T-cell acute lymphoblastic leukemia (T-ALL) that expresses a phosphorylated IRAK molecule selected from the group consisting of p-IRAK-1 phosphorylated at serine 376, p-IRAK-4 phosphorylated at serine 346, p-IRAK-4 phosphorylated at threonine 342, p-IRAK-4 phosphorylated at threonine 345, and p-IRAK-4 phosphorylated at any combination of both serine 346, and threonine 342 or threonine 345, wherein the IRAK-1,-4 inhibitor is a cell-permeable benzimidazole compound that selectively inhibits IRAK-1 and IRAK-4.

2. The method of claim 1 wherein the melanoma or T-cell acute lymphoblastic leukemia (T-ALL) expresses IRAK-1 phosphorylated at serine 376.

3. The method of claim 1 wherein the melanoma or T-cell acute lymphoblastic leukemia (T-ALL) expresses IRAK-4 phosphorylated at one or more of serine 346, threonine 342 and threonine 345.

4. The method of claim 3 wherein the melanoma or T-cell acute lymphoblastic leukemia (T-ALL) further expresses IRAK-1 phosphorylated at serine 376.

5. The method of claim 1 wherein the subject is human.

6. The method of claim 1 wherein the subject has melanoma.

7. The method of claim 1 wherein the subject has T-ALL.

8. The method of claim 1 wherein the IRAK-1,-4 inhibitor is administered orally, by injection, parenterally, by inhalation spray, topically, rectally, nasally, buccally, vaginally, or via an implanted reservoir.

9. The method of claim 1, wherein the IRAK-1,-4 inhibitor is administered locally to the site of the melanoma or T-ALL.

10. The method of claim 1, which further comprises administering a cancer chemotherapeutic drug selected from the group consisting of vinblastine, 5'-flurouracil, cisplatin, vemurafenib, ipilimumab, BMS-663513, ABT-737, PF-04929113, 17-AAG (Geldanamycin), 17-DMAG, BIIB021, BIIB021, SNX-2112, Vinflunine Tartrate, CYT997, Vincristine Sulfate, ABT-751, Docetaxel, Epothilone A, Paclitaxel (Taxol), Vinorelbine (Navelbine), Abiraterone Acetate, B16727, Eplerenone, KX2-391, and Irinotecan Hcl Trihydrate.

11. The method of claim 10, wherein the chemotherapeutic drug is administered in an amount of from about 3.7 mg/m$^2$ to about 100 mg/m$^2$.

* * * * *

SEQUENCE LISTING

<160> NUMBER OF SEQ ID NOS: 16

<210> SEQ ID NO 1

```
<211> LENGTH: 22
<212> TYPE: DNA
<213> ORGANISM: Artificial Sequence
<220> FEATURE:
<223> OTHER INFORMATION: Synthetic: CDKN1C forward primer

<400> SEQUENCE: 1
agatcagcgc ctgagaagtc gt                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic: CDKN1C reverse primer

<400> SEQUENCE: 2
tcggggctct ttgggctcta aa                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic: COLIA1 forward primer

<400> SEQUENCE: 3
gattccctgg acctaaaggt gc                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic: COLIA1 reverse primer

<400> SEQUENCE: 4
agcctctcca tctttgccag ca                                              22

<210> SEQ ID NO 5
<211> LENGTH: 22
<212> TYPE: DNA
<213> ORGANISM: Artificial Sequence
<220> FEATURE:
<223> OTHER INFORMATION: Synthetic: EGR1 forward primer

<400> SEQUENCE: 5
agcagcacct tcaaccctca gg                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic: EGR1 reverse primer

<400> SEQUENCE: 6
gagtggtttg gctggggtaa ct                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic: ID1 forward primer

<400> SEQUENCE: 7
```
gttggagctg aactcggaat cc                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic: ID1 reverse primer

<400> SEQUENCE: 8
acacaagatg cgatcgtccg ca                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic: PLAU1 forward primer

<400> SEQUENCE: 9
ggcttaactc caacacgcaa gg                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic: PLAU1 reverse primer

<400> SEQUENCE: 10
cctccttgga acggatcttc ag                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic: SERPINE1 forward primer

<400> SEQUENCE: 11
ctcatcagcc actggaaagg ca                                              22

<210> SEQ ID NO 12
<211> LENGTH: 23
<212> TYPE: DNA
<213> ORGANISM: Artificial Sequence
<220> FEATURE:
<223> OTHER INFORMATION: Synthetic: SERPINE1 reverse primer

<400> SEQUENCE: 12
gactcgtgaa gtcagcctga aac                                             23

<210> SEQ ID NO 13
<211> LENGTH: 22
<212> TYPE: DNA
<213> ORGANISM: Artificial Sequence
<220> FEATURE:
<223> OTHER INFORMATION: Synthetic: GAPDH forward primer

<400> SEQUENCE: 13
gtctcctctg acttcaacag cg                                              22

<210> SEQ ID NO 14
<211> LENGTH: 22
<212> TYPE: DNA

```
<213> ORGANISM: Artificial Sequence
<220> FEATURE:
<223> OTHER INFORMATION: Synthetic: GAPDH reverse primer

<400> SEQUENCE: 14
accaccctgt tgctgtagcc aa                                              22

<210> SEQ ID NO 15
<211> LENGTH: 22
<212> TYPE: DNA
<213> ORGANISM: Artificial Sequence
<220> FEATURE:
<223> OTHER INFORMATION: Synthetic: Beta-ACTIN forward primer

<400> SEQUENCE: 15
aactcctgct ggacagacga tg                                              22

<210> SEQ ID NO 16
<211> LENGTH: 23
<212> TYPE: DNA
<213> ORGANISM: Artificial Sequence
<220> FEATURE:
<223> OTHER INFORMATION: Synthetic: Beta-ACTIN reverse primer

<400> SEQUENCE: 16
gatcagtgcc atgttccagc aac                                             23
```